US012773312B2

(12) United States Patent
Yohanan et al.

(10) Patent No.: US 12,773,312 B2
(45) Date of Patent: Oct. 27, 2026

(54) PROSTHETIC HEART VALVE LEAFLET ASSEMBLIES AND METHODS

(71) Applicant: EDWARDS LIFESCIENCES CORPORATION, Irvine, CA (US)

(72) Inventors: Ziv Yohanan, Kfar Hahoresh (IL); Elena Sherman, Pardes Hana (IL)

(73) Assignee: Edwards Lifesciences Corporation, Irvine, CA (US)

( * ) Notice: Subject to any disclaimer, the term of this patent is extended or adjusted under 35 U.S.C. 154(b) by 741 days.

(21) Appl. No.: 18/124,688

(22) Filed: Mar. 22, 2023

(65) Prior Publication Data

US 2023/0225862 A1 Jul. 20, 2023

Related U.S. Application Data

(63) Continuation of application No. PCT/US2021/052574, filed on Sep. 29, 2021.

(Continued)

(51) Int. Cl.
*A61F 2/24* (2006.01)

(52) U.S. Cl.
CPC .......... *A61F 2/2418* (2013.01); *A61F 2/2415* (2013.01); *A61F 2220/0075* (2013.01); *A61F 2250/001* (2013.01)

(58) Field of Classification Search
CPC .... A61F 2/24; A61F 2/2418; A61F 2250/001; A61F 2220/0091
See application file for complete search history.

(56) References Cited

U.S. PATENT DOCUMENTS 3,409,013 A 11/1968 Berry
3,548,417 A 12/1970 Ronnie et al.

(Continued)

FOREIGN PATENT DOCUMENTS

DE 0144167 C 9/1903
DE 2246526 A1 3/1973

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Suzette J Gherbi

(74) *Attorney, Agent, or Firm* — Klarquist Sparkman, LLP; Joel B. German

(57) ABSTRACT

A prosthetic heart valve comprises an annular frame comprising a plurality of interconnected struts, wherein the frame is radially compressible and expandable between a radially compressed state and a radially expanded state. A plurality of leaflets are situated within the frame, each leaflet comprising a main body, two opposing commissure tabs arranged on opposite sides of the main body and two opposing sub-commissure tabs arranged on opposite sides of the main body. Each commissure tab of a leaflet is paired with an adjacent commissure tab of an adjacent leaflet to form a commissure that is coupled to the frame. Each sub-commissure tab is paired with an adjacent sub-commissure tab of an adjacent leaflet and connected thereto, wherein each pair of sub-commissure tabs extends radially inwardly relative to the frame.

30 Claims, 11 Drawing Sheets

Related U.S. Application Data

(60) Provisional application No. 63/085,444, filed on Sep. 30, 2020.

(56) References Cited

U.S. PATENT DOCUMENTS 3,587,115 A 6/1971 Donald
3,657,744 A 4/1972 Ersek
3,671,979 A 6/1972 Moulopoulos
3,714,671 A 2/1973 Edwards et al.
3,755,823 A 9/1973 Hancock
4,035,849 A 7/1977 Angell et al.
4,056,854 A 11/1977 Boretos et al.
4,106,129 A 8/1978 Carpentier et al.
4,222,126 A 9/1980 Boretos et al.
4,265,694 A 5/1981 Boretos et al.
4,297,749 A 11/1981 Davis et al.
4,339,831 A 7/1982 Johnson
4,343,048 A 8/1982 Ross et al.
4,345,340 A 8/1982 Rosen
4,373,216 A 2/1983 Klawitter
4,406,022 A 9/1983 Roy
4,441,216 A 4/1984 Ionescu et al.
4,470,157 A 9/1984 Love
4,535,483 A 8/1985 Klawitter et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,820,299 A 4/1989 Philippe et al.
4,829,990 A 5/1989 Thuroff et al.
4,851,001 A 7/1989 Taheri
4,856,516 A 8/1989 Hillstead
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,152,771 A 10/1992 Sabbaghian et al.
5,163,953 A 11/1992 Vince
5,167,628 A 12/1992 Boyles
5,192,297 A 3/1993 Hull
5,266,073 A 11/1993 Wall
5,282,847 A 2/1994 Trescony et al.
5,295,958 A 3/1994 Shturman
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,552 A 5/1995 Andersen et al.
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,558,644 A 9/1996 Boyd et al.
5,571,175 A 11/1996 Vanney et al.
5,584,803 A 12/1996 Stevens et al.
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,792 A 5/1997 Lentell
5,639,274 A 6/1997 Fischell et al.
5,665,115 A 9/1997 Cragg
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,925,063 A 7/1999 Khosravi
5,957,949 A 9/1999 Leonhardt et al.
6,027,525 A 2/2000 Suh et al.
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,102 B1 6/2001 Jayaraman
6,299,637 B1 10/2001 Shaolian et al.
6,302,906 B1 10/2001 Goicoechea et al.
6,338,740 B1 1/2002 Carpentier
6,350,277 B1 2/2002 Kocur
6,352,547 B1 3/2002 Brown et al.
6,425,916 B1 7/2002 Garrison et al.
6,440,764 B1 8/2002 Focht et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.
6,527,979 B2 3/2003 Constantz et al.
6,569,196 B1 5/2003 Vesely
6,582,462 B1 6/2003 Andersen et al.
6,605,112 B1 8/2003 Moll et al.
6,652,578 B2 11/2003 Bailey et al.
6,689,123 B2 2/2004 Pinchasik
6,716,244 B2 4/2004 Klaco
6,730,118 B2 5/2004 Spenser et al.
6,733,525 B2 5/2004 Yang et al.
6,767,362 B2 7/2004 Schreck
6,769,161 B2 8/2004 Brown et al.
6,783,542 B2 8/2004 Eidenschink
6,830,584 B1 12/2004 Seguin
6,878,162 B2 4/2005 Bales et al.
6,893,460 B2 5/2005 Spenser et al.
6,908,481 B2 6/2005 Cribier
6,936,067 B2 8/2005 Buchanan
7,018,406 B2 3/2006 Seguin et al.
7,018,408 B2 3/2006 Bailey et al.
7,096,554 B2 8/2006 Austin et al.
7,225,518 B2 6/2007 Eidenschink et al.
7,276,078 B2 10/2007 Spenser et al.
7,276,084 B2 10/2007 Yang et al.
7,316,710 B1 1/2008 Cheng et al.
7,318,278 B2 1/2008 Zhang et al.
7,374,571 B2 5/2008 Pease et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.

(56) References Cited

U.S. PATENT DOCUMENTS 7,585,321 B2 9/2009 Cribier
7,618,446 B2 11/2009 Andersen et al.
7,618,447 B2 11/2009 Case et al.
7,655,034 B2 2/2010 Mitchell et al.
7,785,366 B2 8/2010 Maurer et al.
7,914,569 B2* 3/2011 Nguyen ................ A61F 2/2418 623/2.12
7,959,665 B2 6/2011 Pienknagura
7,959,672 B2 6/2011 Salahieh et al.
7,993,394 B2 8/2011 Hariton et al.
8,029,556 B2 10/2011 Rowe
8,075,611 B2 12/2011 Millwee et al.
8,128,686 B2 3/2012 Paul et al.
8,167,932 B2 5/2012 Bourang et al.
8,291,570 B2 10/2012 Eidenschink et al.
8,348,998 B2 1/2013 Pintor et al.
8,449,606 B2 5/2013 Eliasen et al.
8,454,685 B2 6/2013 Hariton et al.
8,652,203 B2 2/2014 Quadri et al.
8,685,055 B2 4/2014 VanTassel et al.
8,747,463 B2 6/2014 Fogarty et al.
9,078,781 B2 7/2015 Ryan et al.
11,224,509 B2 1/2022 Dasi et al.
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0143390 A1 10/2002 Ishii
2002/0173842 A1 11/2002 Buchanan
2003/0014105 A1 1/2003 Cao
2003/0040791 A1 2/2003 Oktay
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0024452 A1 2/2004 Kruse et al.
2004/0039436 A1 2/2004 Spenser et al.
2004/0078074 A1 4/2004 Anderson et al.
2004/0186558 A1 9/2004 Pavcnik et al.
2004/0186563 A1 9/2004 Lobbi
2004/0186565 A1 9/2004 Schreck
2004/0260389 A1 12/2004 Case et al.
2005/0010285 A1 1/2005 Lambrecht et al.
2005/0075725 A1 4/2005 Rowe
2005/0075728 A1 4/2005 Nguyen et al.
2005/0096736 A1 5/2005 Osse et al.
2005/0096738 A1 5/2005 Cali et al.
2005/0137686 A1 6/2005 Salahieh et al.
2005/0137699 A1* 6/2005 Salahieh ............... A61F 2/2418 623/2.11
2005/0188525 A1 9/2005 Weber et al.
2005/0203614 A1 9/2005 Forster et al.
2005/0203617 A1 9/2005 Forster et al.
2005/0234546 A1 10/2005 Nugent et al.
2006/0004469 A1 1/2006 Sokel
2006/0025857 A1 2/2006 Bergheim et al.
2006/0058872 A1 3/2006 Salahieh et al.
2006/0074484 A1 4/2006 Huber
2006/0108090 A1 5/2006 Ederer et al.
2006/0149350 A1 7/2006 Patel et al.
2006/0183383 A1 8/2006 Asmus et al.
2006/0229719 A1 10/2006 Marquez et al.
2006/0259136 A1 11/2006 Nguyen et al.
2006/0259137 A1 11/2006 Artof et al.
2006/0287717 A1 12/2006 Rowe et al.
2007/0005131 A1 1/2007 Taylor
2007/0010876 A1 1/2007 Salahieh et al.
2007/0010877 A1 1/2007 Salahieh et al.
2007/0112422 A1 5/2007 Dehdashtian
2007/0162102 A1 7/2007 Ryan et al.
2007/0203503 A1 8/2007 Salahieh et al.
2007/0203575 A1 8/2007 Forster et al.
2007/0203576 A1 8/2007 Lee et al.
2007/0208550 A1 9/2007 Cao et al.
2007/0213813 A1 9/2007 Segesser et al.
2007/0233228 A1 10/2007 Eberhardt et al.
2007/0260305 A1 11/2007 Drews et al.
2007/0265700 A1 11/2007 Eliasen et al.
2008/0021546 A1 1/2008 Patz et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0208327 A1 8/2008 Rowe
2008/0243245 A1 10/2008 Thambar et al.
2008/0255660 A1 10/2008 Guyenot et al.
2008/0275537 A1 11/2008 Limon
2008/0294248 A1 11/2008 Yang et al.
2009/0118826 A1 5/2009 Khaghani
2009/0125118 A1 5/2009 Gong
2009/0157175 A1 6/2009 Benichou
2009/0276040 A1 11/2009 Rowe et al.
2009/0281619 A1 11/2009 Le et al.
2009/0287296 A1 11/2009 Manasse
2009/0287299 A1 11/2009 Tabor et al.
2009/0299452 A1 12/2009 Eidenschink et al.
2009/0319037 A1 12/2009 Rowe et al.
2010/0004735 A1 1/2010 Yang et al.
2010/0049313 A1 2/2010 Alon et al.
2010/0082094 A1 4/2010 Quadri et al.
2010/0100176 A1 4/2010 Elizondo et al.
2010/0168844 A1 7/2010 Toomes et al.
2010/0185277 A1* 7/2010 Braido ...................... A61F 2/89 623/2.37
2010/0198347 A1 8/2010 Zakay et al.
2010/0204781 A1 8/2010 Alkhatib
2011/0015729 A1 1/2011 Jimenez et al.
2011/0022157 A1 1/2011 Essinger et al.
2011/0066224 A1 3/2011 White
2011/0137397 A1 6/2011 Chau et al.
2011/0218619 A1 9/2011 Benichou et al.
2011/0319991 A1 12/2011 Hariton et al.
2012/0030090 A1 2/2012 Johnston et al.
2012/0089223 A1 4/2012 Nguyen et al.
2012/0101571 A1 4/2012 Thambar et al.
2012/0123529 A1* 5/2012 Levi ...................... A61F 2/2418 623/2.11
2012/0259409 A1* 10/2012 Nguyen ................ A61F 2/2415 623/2.15
2013/0023985 A1 1/2013 Khairkhahan et al.
2013/0046373 A1 2/2013 Cartledge et al.
2013/0150956 A1* 6/2013 Yohanan ............... A61F 2/2433 623/2.14
2013/0166017 A1 6/2013 Cartledge et al.
2013/0190857 A1 7/2013 Mitra et al.
2013/0274873 A1 10/2013 Delaloye et al.
2013/0310926 A1 11/2013 Hariton
2013/0317598 A1 11/2013 Rowe et al.
2013/0331929 A1 12/2013 Mitra et al.
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277417 A1 9/2014 Schraut et al.
2014/0277419 A1 9/2014 Garde et al.
2014/0277424 A1 9/2014 Oslund
2014/0277563 A1 9/2014 White
2014/0296962 A1 10/2014 Cartledge et al.
2014/0330372 A1 11/2014 Weston et al.
2014/0343670 A1 11/2014 Bakis et al.
2014/0343671 A1 11/2014 Yohanan et al.
2014/0350667 A1 11/2014 Braido et al.
2015/0073545 A1 3/2015 Braido
2015/0073546 A1 3/2015 Braido
2015/0135506 A1 5/2015 White
2015/0157455 A1 6/2015 Hoang et al.
2016/0374802 A1 12/2016 Levi et al.
2017/0014229 A1* 1/2017 Nguyen-Thien-Nhon .................. A61F 2/2418
2018/0028310 A1 2/2018 Gurovich et al.
2018/0153689 A1 6/2018 Maimon et al.
2018/0325665 A1* 11/2018 Gurovich .............. A61F 2/2418
2018/0344456 A1* 12/2018 Barash .................. A61F 2/2418
2019/0159894 A1 5/2019 Levi et al.

(56) References Cited

U.S. PATENT DOCUMENTS

| | | | | |
|---|---|---|---|---|
| 2019/0192288 | A1 | 6/2019 | Levi et al. | |
| 2019/0192289 | A1 | 6/2019 | Levi et al. | |
| 2022/0218468 | A1* | 7/2022 | Hoang | A61F 2/2412 |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | B1 | 5/1988 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | WO-2020180485 | A1 | 9/2020 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the Sapien+cloth trans-catheter heart valve in the Carpentier-Edwards Perimount valves. Eur J Cardiothorac Surg. 2011;40(5): 1120-6. Epub Apr. 7, 2011.

Fontaine, M.D., Arthur B., et al, "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al, "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

PROSTHETIC HEART VALVE LEAFLET ASSEMBLIES AND METHODS

CROSS-REFERENCE TO RELATED APPLICATIONS

The present application is a continuation of PCT Application No. PCT/US2021/052574, filed Sep. 29, 2021, which claims the benefit of U.S. Application No. 63/085,444, filed Sep. 30, 2020, which is incorporated herein by reference.

FIELD

The present disclosure relates generally to prosthetic heart valves, and more particularly to leaflet assemblies for prosthetic heart valves and methods for their assembly.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. The leaflets may be attached to the frame at commissure tabs (also referred to as leaflet tabs) of the leaflets. For example, a commissure may be formed by connecting the commissure tabs of two adjacent leaflets to one another, and in some embodiments, to an attachment element configured to couple to a commissure support portion of the frame. The commissure or the attachment element can then be attached to the commissure support portion of the frame via a fastener, such as a suture. The cusp edge portions (the inflow edge portions) of the leaflets can be coupled to the frame, such as with a skirt that is sutured to struts of the frame and to the cusp edge portions of the leaflets.

Frames of prosthetic heart valves, in general, are foreshortened when radially expanded and axially elongated when radially compressed. As a result, the leaflets typically are stretched or elongated axially when the frame is radially compressed. To allow for such elongation of the leaflets without damaging the leaflets, the leaflets can include sub-commissure portions located between the commissures and the cusp edge portions that remain unattached to the frame. However, when the frame is radially expanded and the leaflets revert to their undeformed state, folds or slack can form in the unattached sub-commissure portions of the leaflets. These folds can contact the frame when the leaflets open under the pressure of retrograde blood, which can result in abrasion of the leaflets. Moreover, the folds can constrain the extent the leaflets can open under the pressure of retrograde blood, which limits the opening diameter of the leaflets and may result in higher pressure gradients across the prosthetic valve.

Accordingly, a need exists for improved prosthetic heart valve leaflet assemblies, and methods for assembling leaflets to a frame of a prosthetic heart valve.

SUMMARY

Described herein are embodiments of prosthetic heart valves and methods for assembling prosthetic heart valves including an annular frame and leaflet assembly. The frame can be radially expandable and compressible between a radially compressed state and a radially expanded state. The leaflet assembly can comprise a plurality of leaflets coupled to each other to form commissures, which can be coupled to the frame, such as by mounting the commissures to commissure support posts of the frame.

In one representative embodiment, a prosthetic heart valve comprises an annular frame comprising a plurality of interconnected struts, wherein the frame is radially compressible and expandable between a radially compressed state and a radially expanded state; and a plurality of leaflets situated within the frame, each leaflet comprising a main body, two opposing commissure tabs arranged on opposite sides of the main body and two opposing sub-commissure tabs arranged on opposite sides of the main body. Each commissure tab of a leaflet is paired with an adjacent commissure tab of an adjacent leaflet to form a commissure that is coupled to the frame. Each sub-commissure tab is paired with an adjacent sub-commissure tab of an adjacent leaflet and connected thereto, wherein each pair of sub-commissure tabs extends radially inwardly relative to the frame.

In another representative embodiment, a method of assembling a prosthetic heart valve comprises providing a plurality of leaflets, wherein each leaflet comprises a main body, two opposing commissure tabs arranged on opposite sides of the main body and two opposing sub-commissure tabs arranged on opposite sides of the main body; pairing each commissure tab with an adjacent commissure of an adjacent leaflet to form a plurality of commissures, and coupling the commissures to an annular frame, wherein the frame is radially compressible and expandable between a radially compressed state and a radially expanded state; and pairing each sub-commissure tab with an adjacent commissure of an adjacent leaflet, wherein each pair of sub-commissure tabs extends radially inwardly relative to the frame.

In another representative embodiment, a prosthetic heart valve comprises an annular frame comprising a plurality of interconnected struts, wherein the frame is radially compressible and expandable between a radially compressed state and a radially expanded state; and a plurality of leaflets situated within the frame, each leaflet comprising a main body, a cusp edge portion, two opposing commissure tabs arranged on opposite sides of the main body, two sub-commissures edges forming notches on opposite sides of the main body between the commissure tabs and upper end portions of the cusp edge portion, and two opposing sub-commissure tabs arranged on opposite sides of the main body and extending laterally from the sub-commissures edges. Each commissure tab of a leaflet is paired with an adjacent commissure tab of an adjacent leaflet to form a commissure that is coupled to the frame. Each sub-commissure tab is paired with an adjacent sub-commissure tab of an adjacent leaflet and connected thereto.

In another representative embodiment, a method of assembling a prosthetic heart valve comprises providing a plurality of leaflets, wherein each leaflet comprises a main body, a cusp edge portion, two opposing commissure tabs arranged on opposite sides of the main body, two sub-commissures edges forming notches on opposite sides of the main body between the commissure tabs and upper end portions of the cusp edge portion, and two opposing sub-commissure tabs arranged on opposite sides of the main body and extending laterally from the sub-commissures edges; pairing each commissure tab with an adjacent commissure of an adjacent leaflet to form a plurality of commissures, and coupling the commissures to an annular frame, wherein the frame is radially compressible and expandable between a radially compressed state and a radially expanded state; and pairing each sub-commissure tab with an adjacent commissure of an adjacent leaflet and connecting the sub-commissure tabs of each pair to each other.

The foregoing and other objects, features, and advantages of the invention will become more apparent from the following detailed description, which proceeds with reference to the accompanying figures.

DETAILED DESCRIPTION

General Considerations

Figure 1:
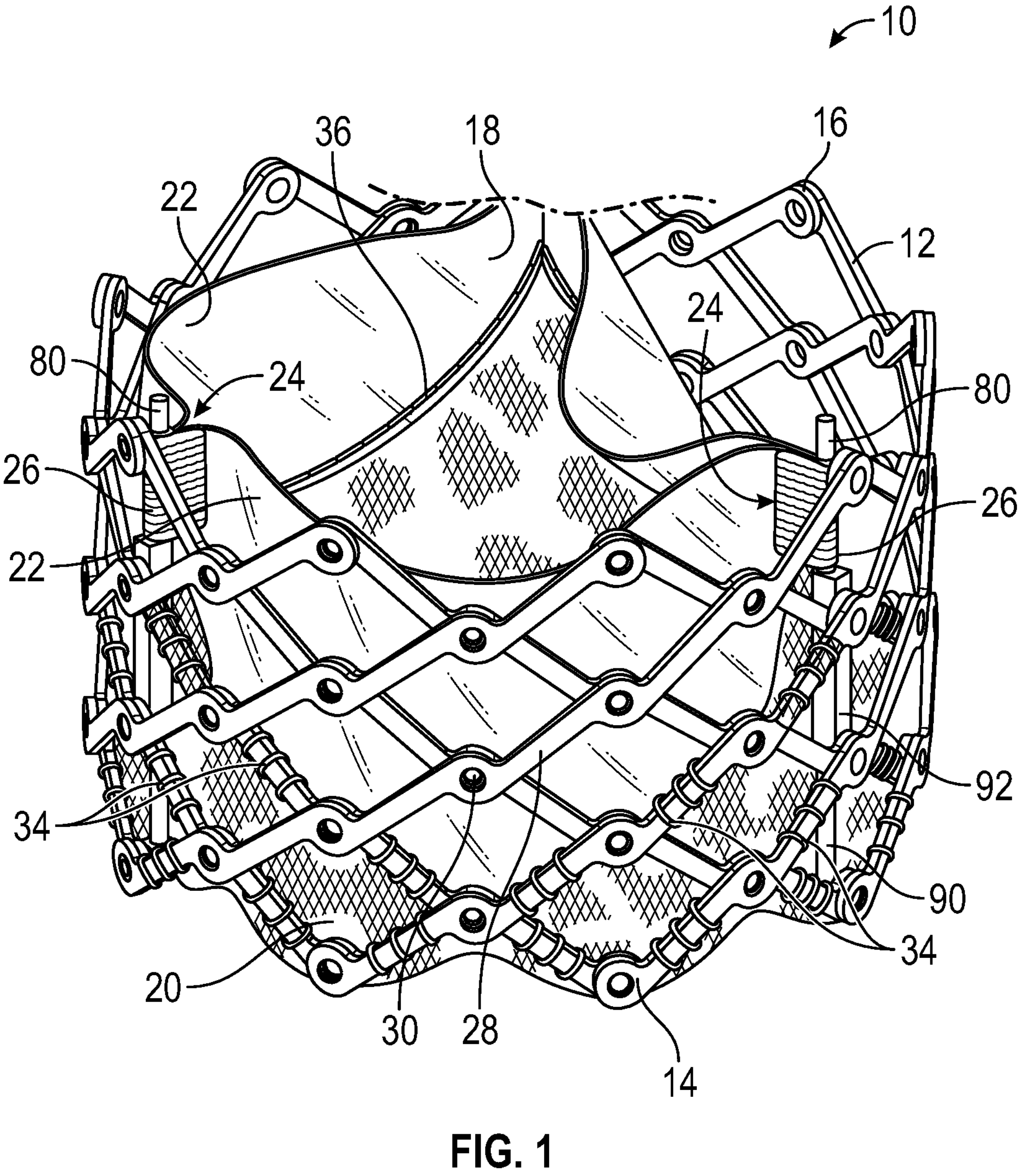
FIG. 1 is a perspective view of an exemplary embodiment of a prosthetic heart valve.

For purposes of this description, certain aspects, advantages, and novel features of examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the prosthetic valves disclosed herein may be used with a variety of implant delivery apparatuses and can be implanted via various delivery procedures, examples of which will be discussed in more detail later.

FIG. 1 shows an exemplary prosthetic heart valve 10, according to one example. The prosthetic heart valve 10 can be radially compressible and expandable between a radially compressed configuration for delivery into a patient and a radially expanded configuration.

Any of the prosthetic valves disclosed herein are adapted to be implanted in the native aortic annulus, although in other examples they can be adapted to be implanted in the other native annuluses of the heart (the pulmonary, mitral, and tricuspid valves). The disclosed prosthetic valves also can be implanted within vessels communicating with the heart, including a pulmonary artery (for replacing the function of a diseased pulmonary valve, or the superior vena cava or the inferior vena cava (for replacing the function of a diseased tricuspid valve) or various other veins, arteries and vessels of a patient. The disclosed prosthetic valves also can be implanted within a previously implanted prosthetic valve (which can be a prosthetic surgical valve or a prosthetic transcatheter heart valve) in a valve-in-valve procedure.

In some examples, the disclosed prosthetic valves can be implanted within a docking or anchoring device that is implanted within a native heart valve or a vessel. For example, in one example, the disclosed prosthetic valves can be implanted within a docking device implanted within the pulmonary artery for replacing the function of a diseased pulmonary valve, such as disclosed in U.S. Publication No. 2017/0231756, which is incorporated by reference herein. In another example, the disclosed prosthetic valves can be implanted within a docking device implanted within or at the native mitral valve, such as disclosed in PCT Publication No. WO2020/247907, which is incorporated herein by reference. In another example, the disclosed prosthetic valves can be implanted within a docking device implanted within the superior or inferior vena cava for replacing the function of a diseased tricuspid valve, such as disclosed in U.S. Publication No. 2019/0000615, which is incorporated herein by reference.

The prosthetic heart valve 10 can include an annular stent or frame 12 having a first end 14 and a second end 16. In the depicted embodiment, the first end 14 is an inflow end and the second end 16 is an outflow end. The outflow end 16 can be coupled to a delivery apparatus for delivering and implanting the prosthetic heart valve within the native aortic valve is a transfemoral, retrograde delivery approach. Thus, in the delivery configuration of the prosthetic heart valve, the outflow end 16 is the proximal-most end of the prosthetic valve. In other embodiments, the inflow end 14 can be coupled to the delivery apparatus, depending on the particular native valve being replaced and the delivery technique that is used (e.g., trans-septal, transapical, etc.). For example, the inflow end 14 can be coupled to the delivery apparatus (and therefore is the proximal-most end of the prosthetic heart valve in the delivery configuration) when delivering the prosthetic heart valve to the native mitral valve via a trans-septal delivery approach.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic heart valve 10 when the prosthetic heart valve 10 is in the expanded configuration. In other implementations, the struts 28 can be offset by a different amount than depicted in FIG. 1, or some or all of the struts 28 can be positioned parallel to the longitudinal axis of the prosthetic heart valve 10.

In the illustrated embodiment, the struts 28 are pivotably coupled to one another at one or more pivot joints along the length of each strut. For example, in the illustrated configuration, each of the struts 28 can be formed with apertures at opposing ends of the strut and apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic heart valve 10. In some embodiments, a pivot joint can comprise a rivet or pin 30 that extends through apertures of an inner strut and an outer strut that overlaps the inner strut at the pivot joint. In other embodiments, a pivot joint can comprise a rivet or pin 30 that is integrally formed on one of the inner or outer struts and extends through an aperture in the other one of the inner and outer strut.

Figure 2A:
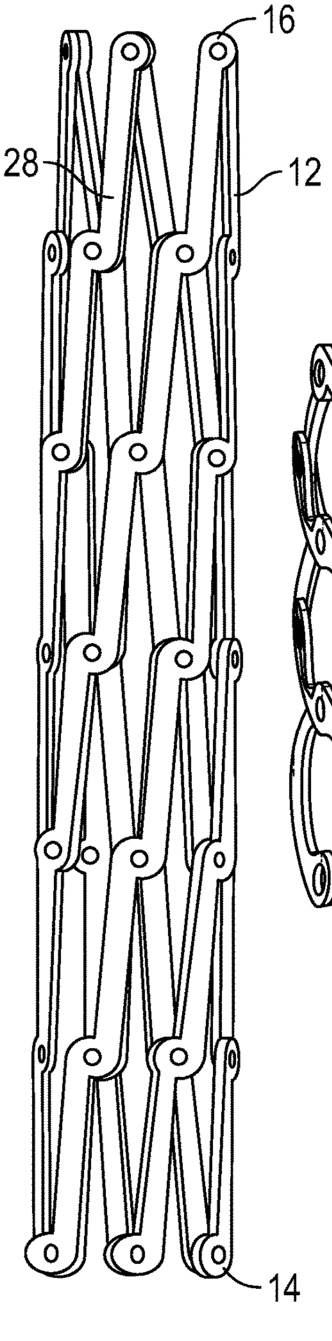
FIG. 2A is a side view of the frame of the prosthetic valve of FIG. 1 shown in a radially compressed state.
Figure 2B:
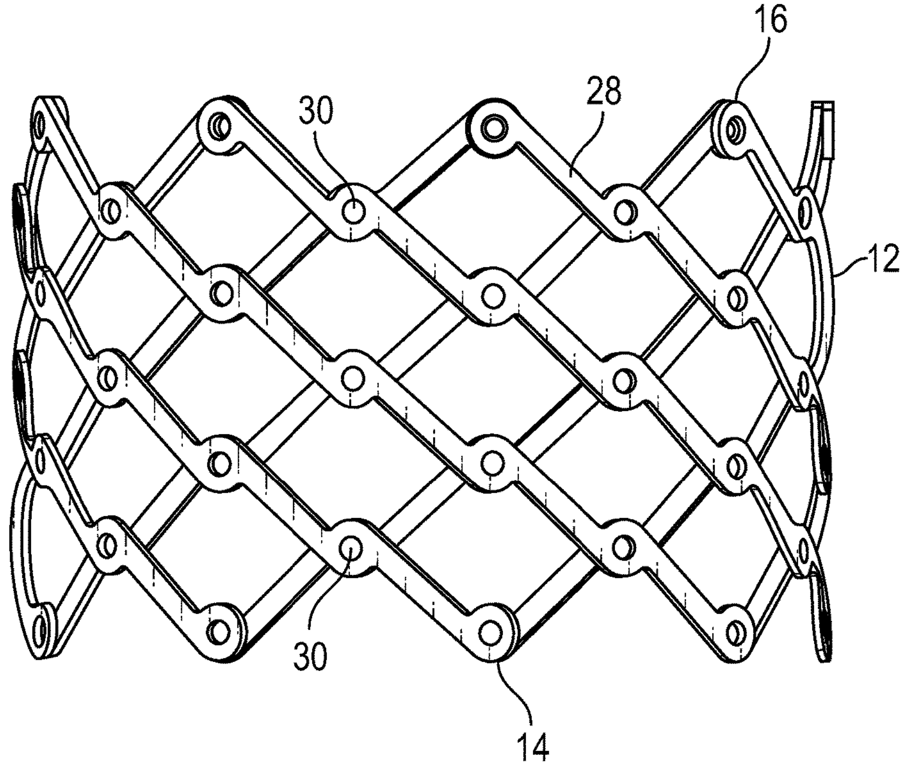
FIG. 2B is a side view of the frame of the prosthetic valve of FIG. 1 shown in a radially expanded state.

FIG. 2A shows the frame 12 of the prosthetic valve in a radially compressed state and FIG. 2B shows the frame of the prosthetic valve in a radially expanded state. As shown, when radially compressed, the frame 12 elongates axially, and when radially expanded, the frame 12 foreshortens.

In some embodiments, the frame 12 can be constructed by forming individual components (e.g., the struts and fasteners of the frame) and then mechanically assembling and connecting the individual components together. Further details regarding the construction of the frame and the prosthetic heart valve are described in U.S. Patent Application Publication Nos. 2018/0153689, 2018/0344456, 2019/0060057, and 2019/0105153, and U.S. patent application Ser. No. 16/788,090, filed Feb. 11, 2020, and 62/945,000, filed Dec. 6, 2019, all of which are incorporated herein by reference.

In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Examples of such frames are disclosed in U.S. Pat. No. 9,393,110 and U.S. Publication No. 2018/0028310, which are incorporated herein by reference.

The prosthetic heart valve 10 can also include a valvular structure 18 which is coupled to the frame 12 and configured to regulate the flow of blood through the prosthetic heart valve 10 from the inflow end 14 to the outflow end 16. The prosthetic heart valve 10 can further include a plurality of actuators 80 mounted to and equally spaced around the inner surface of the frame 12. The actuators are configured to apply expansion and compression to the frame for radially expanding and compressing the prosthetic valve.

In the illustrated embodiment, the actuators 80 are linear actuators, each of which comprises an inner member, or piston, 90 and an outer member, or cylinder, 92. The inner member 90 is pivotably coupled to a junction of the frame, such as at the first end 14, while the outer member 92 is pivotably coupled to another junction of the frame closer to the second end 16. Moving the inner member 90 proximally relative to the outer member 92 and/or moving the outer member 92 distally relative to the inner member 90 is effective to radially expand the prosthetic valve. Conversely, moving the inner member 90 distally relative to the outer member 92 and/or moving the outer member 92 proximally relative to the inner member 90 is effective to radially compress the prosthetic valve. The actuators 80 can include locking mechanisms that are configured to retain the prosthetic valve in an expanded state inside the patient's body.

In some embodiments, each of the actuators 80 can be configured to form a releasable connection with one or more respective actuators of a delivery apparatus of a transcatheter delivery system. The actuators of the delivery apparatus can transmit forces from a handle of the delivery apparatus to the actuators 80 for expanding or compressing the prosthetic valve. Further details of the actuators, locking mechanisms and delivery apparatuses for actuating the actuators can be found in U.S. Patent Application Publication Nos. 2018/0153689, 2019/0060057 and 2018/0325665, U.S. Application No. 62/990,299, filed Mar. 16, 2020, and PCT Application No. PCT/US2021/022467, filed Mar. 16, 2021, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

In some embodiments, each of the actuators 80 can be used to support a respective commissure 24 (described below). As such, the actuators 80 can include commissure support portions for supporting and attaching commissures 24 of the valvular structure 18 to the frame 12, as described further herein.

The valvular structure 18 can include, for example, a leaflet assembly comprising one or more leaflets 22 (three leaflets 22 in the illustrated embodiment) made of a flexible material. The leaflets 22 of the leaflet assembly can be made from in whole or part, biological material, bio-compatible synthetic materials, or other such materials. Suitable biological material can include, for example, bovine pericardium (or pericardium from other sources). Each leaflet 22 includes two opposing commissure tabs arranged on opposite sides of a body of the leaflet. The body of the leaflet may be the portion of the leaflet that is adapted to bend and move during operation of the prosthetic heart valve 10. The commissure tabs of adjacent leaflets 22 can be arranged to form commissures 24, which can be, for example, mounted to commissure support portions of respective actuators 80.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, U.S. Publication Nos. 2018/0325665, 2019/0105153, and 2019/0192296, U.S. Patent Application Nos. 62/797,837, filed Jan. 28, 2019, 62/823,905, filed Mar. 26, 2019, 62/854,702, filed May 30, 2019, 62/928,993, filed Oct. 31, 2019, 62/959,723, filed Jan. 10, 2020, 62/971,011, filed Feb. 6, 2020, 62/985,558, filed Mar. 5, 2020, and 62/960,838, filed Jan. 14, 2020, and PCT Application Nos. PCT/US2019/61392, filed Nov. 14, 2019, PCT/US2020/18664, filed Feb. 18, 2020, all of which are incorporated herein by reference in their entireties.

In some embodiments, as shown in FIG. 1, the commissures 24 can be mounted (e.g., sutured) directly to commissure support portions of the actuators 80 of the frame 12 via commissure attachment elements 26, which can be a piece of cloth or fabric. As one example, the commissure attachment elements 26 may include one or more stitches securing the commissures 24 to corresponding actuators 80. In other embodiments, the commissures 24 can be mounted to support struts or posts of the frame that are separate from the actuators 80. In still other embodiments, the commissures may be secured to an additional commissure attachment or support member (as described further herein) and the support member is then secured to a commissure support portion of an actuator 80 or support struts or posts of the frame.

The prosthetic heart valve 10 can also include one or more skirts or sealing members. For example, as shown in FIG. 1, the prosthetic heart valve 10 can include an inner skirt 20 mounted on the inner surface of the frame 12. As shown in FIG. 1, the inner skirt 20 is a circumferential inner skirt that spans an entire circumference of the inner surface of the frame 12. The inner skirt 20 can function as a sealing member to prevent or decrease perivalvular leakage (e.g., when the valve is placed at the implantation site) and as an attachment surface to anchor the leaflets 22 to the frame 12. For example, the inflow (e.g., cusp) edges of the leaflets 22 can be sutured directly to the inner skirt 20 along a stitching line 36 (which can be referred to as a "scallop line"). The inner skirt 20 in turn can be directly connected to selected struts 28 of the frame, such as with sutures 34, as shown in FIG. 1.

The prosthetic heart valve 10 can also include an outer skirt mounted on the outer surface of the frame 12 (not shown in FIG. 1). The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., polyethylene terephthalate (PET)) or natural tissue (e.g., pericardial tissue). The inner and outer skirts can be mounted to the frame using sutures, an adhesive, welding, and/or other means for attaching the skirts to the frame.

Figure 3:
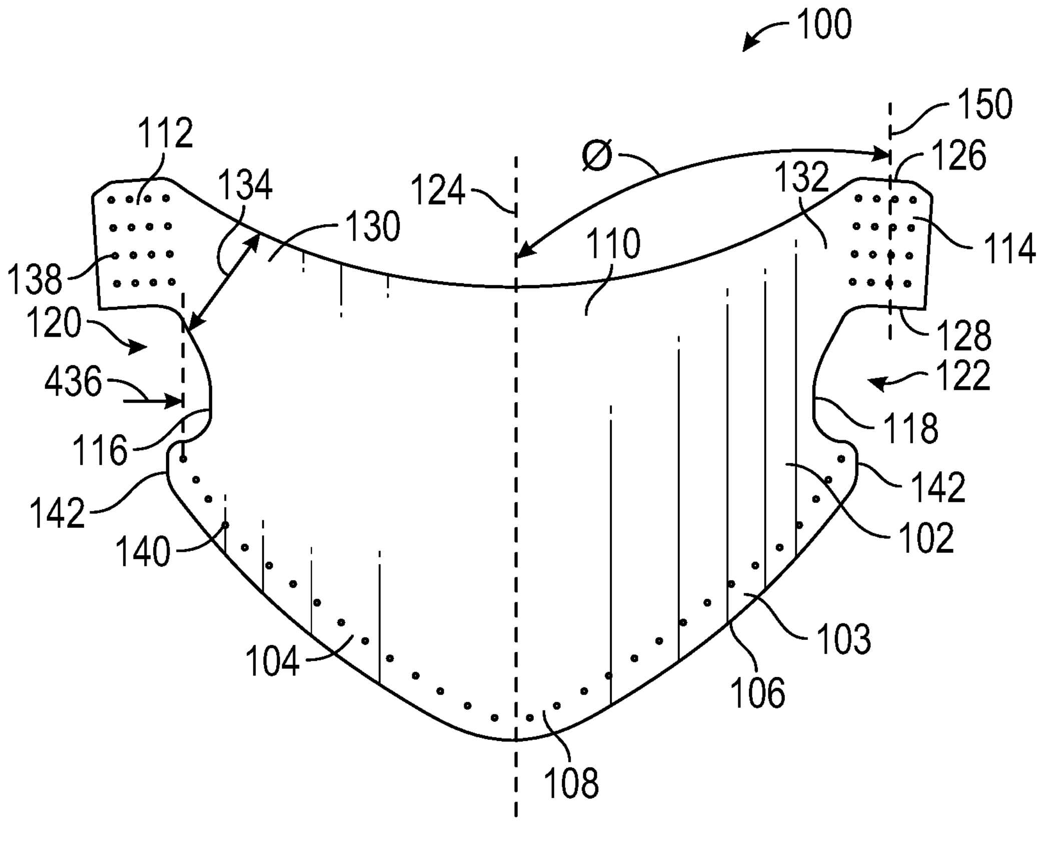
FIG. 3 is a flattened view of one of the leaflets of the prosthetic valve of FIG. 1.

FIG. 3 shows an exemplary leaflet 100 that may be included in a valvular structure of a prosthetic heart valve (e.g., valvular structure 18 of prosthetic heart valve 10 of FIG. 1). The leaflet 100 is laid flat for the purpose of illustration. The leaflet 100 can comprise a main body (e.g., body) 102 with cusp (e.g., inflow) edge portion 103 including a first (left) side cusp edge portion 104 and a second (right) side cusp edge portion 106 which connect together at an inflow-most end portion 108 of the leaflet 100. Together, the first and second cusp edge portions 104 and 106 form a scallop line of the leaflet 100. The upper end portions of the cusp edge portions 104, 106 can form sub-commissure tabs 142. The sub-commissure tabs 142 can be configured for engagement with corresponding sub-commissure tabs of adjacent leaflets to form sub-commissure portions, as further described below.

The leaflet 100 can include commissure tabs 112 and 114, extending from opposite sides of the main body 102. The commissure tabs can be configured for engagement with corresponding commissure tabs of adjacent leaflets to form commissures, and for attachment to the frame of the prosthetic heart valve (e.g., through an attachment member of the commissure, as described further herein). An outflow edge portion 110 extends across the leaflet 100, between the commissure tabs 112 and 114.

A curved edge portion 116, 118 extends between and connects a corresponding one of the commissure tabs 112 and 114 and a corresponding one of the first and second cusp edge portions 104 and 106. Each curved edge portion 116, 118 defines an open region on either side of the leaflet 100, referred to herein as a window or notch 120, 122.

As shown in FIG. 3, each of the first and second cusp edge portions 104 and 106 are angled from a bottom edge of a corresponding one of the curved edge portions 116 and 118 to the inflow end portion 108. An upper edge of each of the first and second cusp edge portions 104 and 106 is arranged inward of an outer edge of a corresponding one of the commissures tabs 112 and 114, in a lateral direction that is arranged perpendicular to an axial direction, the axial direction running from the outflow edge portion 110 to the inflow end portion 108, in parallel to a centerline 124 of the leaflet. As a result, the overall shape of the leaflet is tapered from the outflow edge portion 110 to the inflow end portion 108.

In some embodiments, a shape of the leaflet 100 can be configured such that the commissure tabs 112 and 114 are angled relative to the axial direction which is parallel with the centerline 124 extending through a center of the leaflet 100, between the outflow edge portion 110 and the inflow end portion 108. For example, as shown in FIG. 3, lateral (e.g., upper and lower) edges 126 and 128 of each commissure tab 112, 114 can be angled, at an angle θ, from vertical (e.g., centerline 124). As shown in FIG. 3, the angle θ can be defined between the centerline 124 and line 150 which extends through the commissure tabs 112, 114, perpendicular to the lateral edges 126 and 128.

In some embodiments, the angle θ can be selected to match or be similar to (e.g., within a selected, finite range of) a draft angle of the frame of the prosthetic heart valve. For example, the frame may be tapered from the outflow end to the inflow end of the frame, creating a tapered shape of the frame defined by the draft angle, as further disclosed in U.S. Application No. 63/024,951, filed May 14, 2020, which is incorporated herein by reference. By selecting the angle θ to match or be close to matching (e.g., within 5-10% or within 5% of) the draft angle of the frame, stresses concentrated at the commissure tabs of the commissure may be reduced, while also allowing sufficient opening of the leaflet during operation of the valve, in vivo (e.g., during opening and closing of the leaflet).

In some embodiments, the angle θ can be selected based on the draft angle of the frame and/or based on the geometry of the leaflet, in order to reduce stresses experienced at the commissure while also allowing sufficient opening of the leaflet during valve operation, in vivo. In some embodiments, a tapered frame may facilitate a more cylindrical opening of the leaflets, while maintaining the distance between leaflets and the frame during the open phase (e.g., to reduce or avoid abrasion).

In some embodiments, dimensions of the windows 120 and 122 and/or neck regions 130 and 132 of the leaflet 400 can be selected to maximize a width of the leaflet 100 at each neck region 130, 132, while also minimizing a surface area of each window 120, 122. Each neck region 130, 132 is defined between a corresponding one of the commissure tabs 112 and 114 and the main body 102 of the leaflet 100. For example, in some embodiments, a width 134 of each neck region 130 and 132 and a window width 136 of each window 120 and 122 may be selected to help with leaflet stress distribution during the cyclic loading and unloading (e.g., during closing and opening of the leaflet assembly during valve operation) and decrease tissue strain on the leaflet, in order to increase longevity of the leaflet 100.

In some embodiments, the commissure tabs 112 and 114 can include a plurality of columns or lines of apertures 138, adapted to receive lines of fasteners (e.g., sutures) during folding and securing of the commissure tabs to form commissures (as described further below with reference to FIGS. 4, 5A and 5B). These lines of apertures 138 may be referred to herein as stitching lines. As shown in FIG. 3, each commissure tab 112 and 114 includes four relatively straight stitching lines. However, in alternate embodiments, each commissure tab 112 and 114 can include more or less than four stitching lines (e.g., one, two, three, five, or the like). Further, in some embodiments, instead of a relatively straight stitching line (e.g., with all apertures 138 of the same stitching line arranged in a relatively straight line), one or more of the stitching lines may be non-straight with at least a portion (e.g., one or more apertures 138) that is offset from a remaining portion of the stitching line.

As further shown in FIG. 3, in some embodiments, each of the first and second edge portions 104 and 106 can include a line of apertures 140 adapted to receive a line of fasteners (e.g., sutures) which secures the first and second cusp edge portions 104 and 106 to a skirt (e.g., skirt 20 of FIG. 1) that is configured to be attached to the frame of the prosthetic heart valve. In some embodiments, the skirt may extend from the line of apertures 140 or just above the line of apertures 140 and below (e.g., past) a bottom (inflow) edge of the first and second cusp edge portions 104 and 106.

Other leaflet configurations that may be implemented in any of the prosthetic valves disclosed herein are described in U.S. Publication No. 2018/0028310 and U.S. Application No. 62/978,455, filed Feb. 19, 2020, which are incorporated herein by reference.

Figure 4:
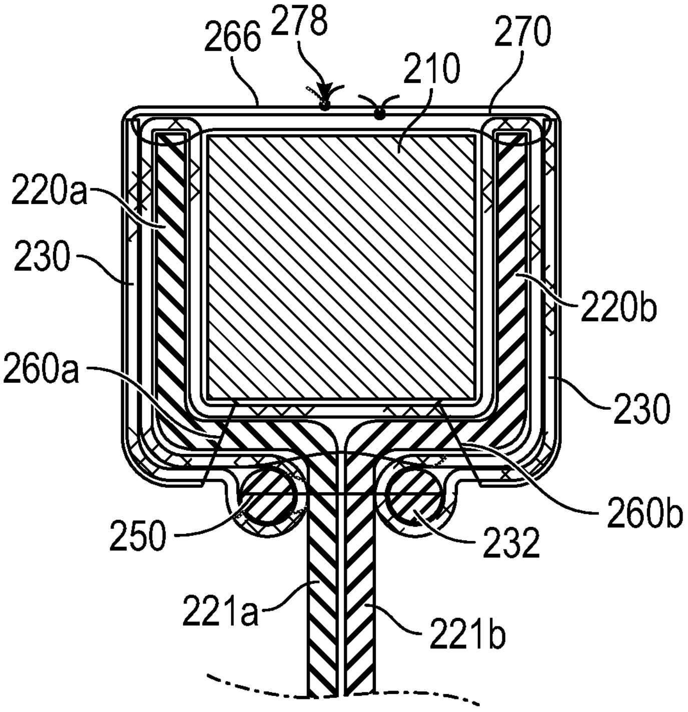
FIG. 4 illustrates a cross-sectional view of an example commissure of a prosthetic valve, in which the commissure is secured to a support post of the prosthetic valve.
Figure 5A:
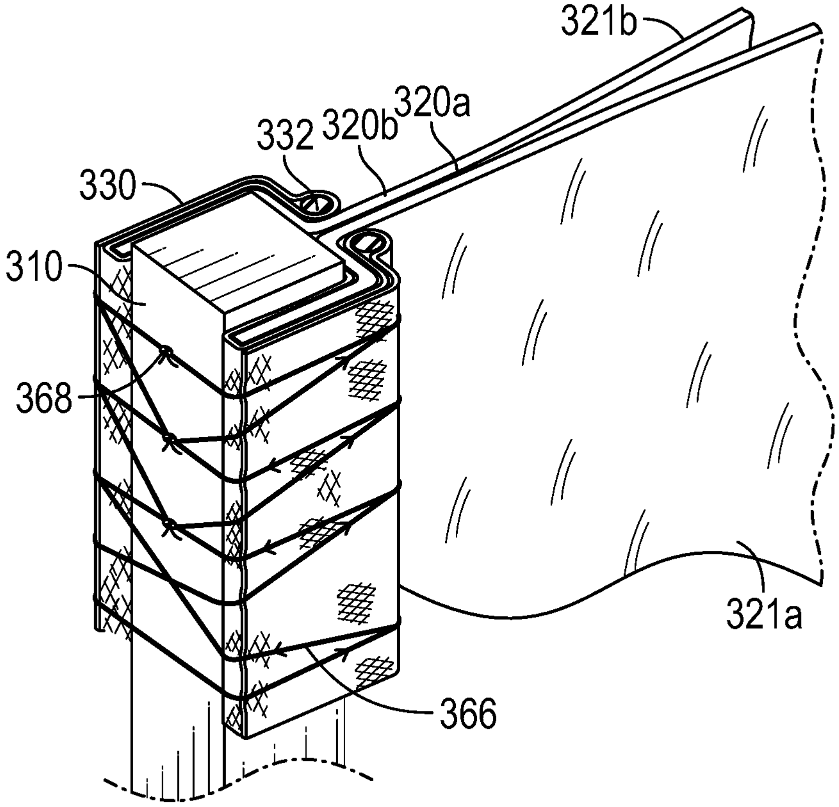
FIGS. 5A and 5B illustrate different views of an example commissure secured to a support structure using suture loops that extend around an outer surface of a support strip of the commissure.
Figure 5B:
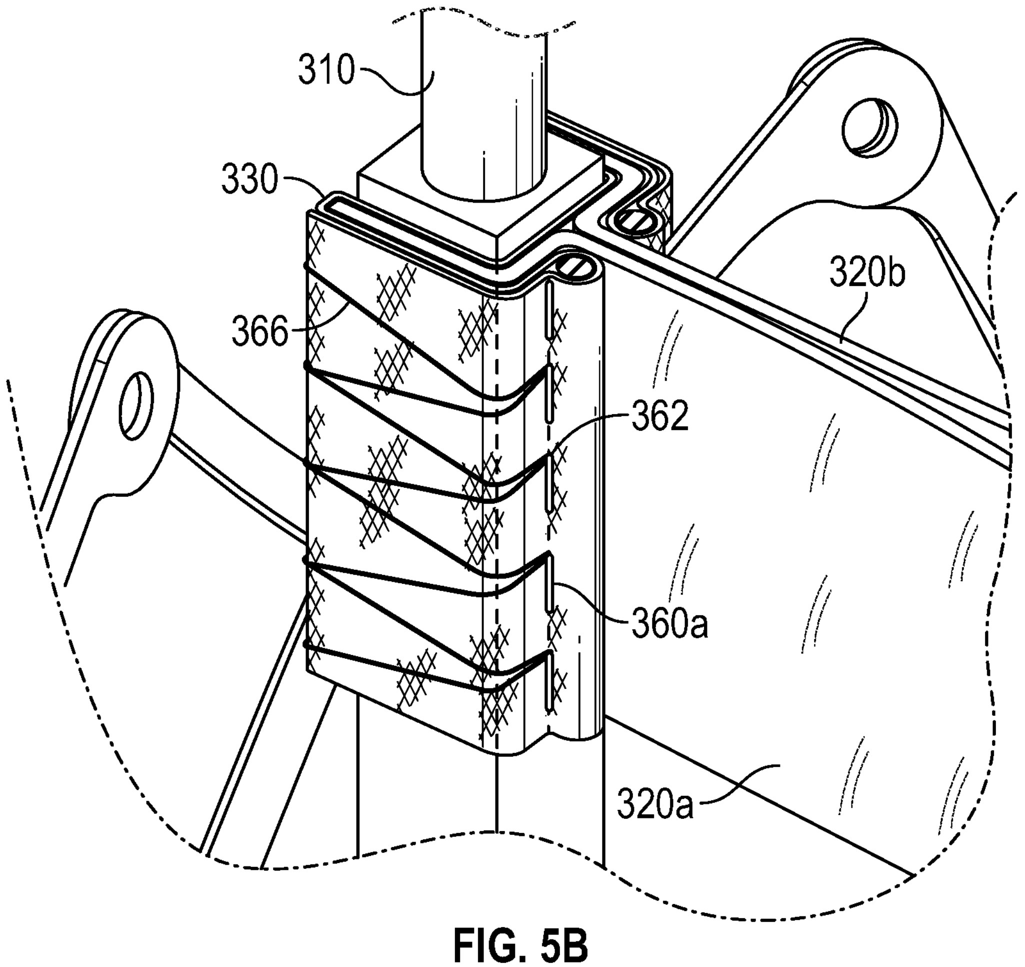

FIGS. 4-5B show example commissure tab assemblies and attachments of commissure tab assemblies to a commissure post or other support structure of a frame of a prosthetic valve. FIG. 4 shows an example cross-sectional view of the commissure tab assembly and FIGS. 5A and 5B show isometric views of an example commissure tab assembly from two different view angles.

A commissure tab assembly may be pre-assembled prior to attachment thereof to the frame by performing a pre-assembly process. The pre-assembly process includes, using the components of FIG. 4 in one example, placing a support strip 230 (which can also be referred to as a reinforcing member) (e.g., a flexible cloth/fabric) over a pair of adjacent commissure tabs 220*a* and 220*b* of respective leaflets 221*a* and 221*b* and folding end portions of the support strip over end portions of the commissure tabs. In some embodiments, the leaflets 221*a*, 221*b* can have the same configuration as leaflet 100, described above, or leaflets 500 or 500' described below, although other leaflet configurations, including any disclosed herein, can be used.

A reinforcing element 232, described in more detail below, may be placed against a surface of the support strip on each opposing side of the support strip, such that at least a portion of the support strip is sandwiched between the reinforcing element 232 and a respective commissure tab 220*a* or 220*b* on each opposing side of the support strip. In order to secure the support strip to the commissure tabs and the reinforcing element, the pre-assembly process may further include extending a primary suture 250 through, in order (or in the reverse order, e.g., starting from the last-listed element and extending through the following list of elements, in reverse, to the first-listed element), a first portion of a reinforcing element 232, a first portion on a first side of a support strip (e.g., a flexible cloth/fabric) 230, a first commissure tab 220*a*, a second commissure tab 220*b* (where commissure tabs 220*a* and 220*b* are two commissure tabs of adjacent leaflets, e.g., leaflets 221*a* and 221*b*), a second portion on a second side of the support strip 230, and a second portion of the reinforcing element 232. The second side of the support strip is opposite the first side relative to a center of the support strip (e.g., a centerline that divides a width/longest dimension of the strip in half).

Although not shown in FIGS. 5A and 5B, it is to be understood that a primary suture may be similarly applied to the commissure assembly shown therein in a similar manner as described above with respect to FIG. 4 (e.g., extending the primary suture through portions of reinforcing elements 332, one or more layers of a support strip 330, and commissure tabs 320*a* and 320*b* of leaflets 321*a* and 321*b*, respectively).

The support strip (e.g., support strip 230 of FIGS. 2 and/or 330 of FIGS. 5A and 5B) may be a strip of any suitable material (e.g., fabric), which may include material that is stronger (e.g., more resilient to tearing and/or deforming) than a material used for forming the leaflets and/or the commissure tab portions of the leaflets of the prosthetic valve. In one example, the support strip is a polyethylene terephthalate (PET) fabric, although various other suitable biocompatible fabrics can be used.

The support strip may be longer in one dimension than another (e.g., having a width/length that is greater than a height of the strip). The support strip may be continuous (e.g., with no gaps and/or having a substantially uniform distribution of the material forming the support strip, other than optional apertures forming the suture lines described herein) and may be relatively thin (e.g., having a thickness that is substantially smaller than the width and height of the strip and substantially smaller than a width or diameter of the reinforcing elements, discussed in more detail below).

The reinforcing elements, such as reinforcing element 232 of FIG. 4 and reinforcing element 332 of FIGS. 5A and 5B, may include a string, a cord, and/or a relatively thick suture (e.g., an Ethibond suture), which may be substantially wider/thicker and/or have a substantially larger diameter (e.g., at least twice as wide/thick and/or have twice the diameter) than stitching sutures (e.g., primary sutures, secondary sutures, described in more detail below, tertiary sutures, described in more detail below, and/or other sutures of the commissure). The reinforcing elements may be substantially the same height (or slightly shorter, such as 1-5% shorter to provide for machining tolerances and avoid extension of the inner reinforcing element past edges of the strip) as the height of the support strip. In other examples, the reinforcing elements can be a relatively narrow strip(s) of fabric, which can be folded lengthwise one or more times to increase its overall thickness. In still other examples, the reinforcing elements can be a metal wire(s) or a bar(s), such as a rectangular or cylindrical bar(s), formed from a metal and/or a polymer.

The reinforcing elements may include two individual reinforcing elements or two portions of a single reinforcing member that extends along outer surfaces of each of the first and the second commissure tabs. For example, a reinforcing member may be folded into a U-shape configuration to form the reinforcing elements (e.g., the reinforcing elements may be individual elements that are coupled to one another and/or form different sections of a single continuous element/member). In other examples, a reinforcing member may be discontinuous and include the reinforcing elements as discrete or separate elements in a spatially separated configuration (e.g., where a first reinforcing element is spatially separated from a second reinforcing element).

In some examples, the reinforcing elements may be aligned with one or more alignment markings and/or suture/stitching lines of the support strip. In some embodiments, the reinforcing elements are placed against outer surfaces of the commissure tabs, respectively, and opposing end or side portions of the support strip are positioned on an opposing side(s) of the reinforcing elements from the respective commissure tabs. For example, each reinforcing element may be sandwiched between a respective portion of the support strip and a respective one of the commissure tabs. In other embodiments, the support strip is at least partially wrapped or folded around the reinforcing elements to at least partially encase the reinforcing elements. In such examples, the portions of the support strip that at least partially encase the reinforcing elements may be placed against the outer surfaces of the commissure tabs, respectively.

Returning to the formation of the pre-assembled commissure, the primary suture 250 may only pass through a single layer of the support strip 230 on either side of the support strip (e.g., a respective layer of the support strip that is positioned between the reinforcing element 232 and a respective one of the commissure tabs 220*a* and 220*b*). In order to increase the strength and force distribution provided by the commissure assembly, end portions of each side of the support strip 230 may be further folded over respective portions of the reinforcing element 232 and positioned alongside the respective end portions of the commissure tabs 220*a* and 220*b* to form an additional layer of support strip on an outer region of the commissure assembly. For example, as shown in FIG. 4, a single layer of the support strip 230 may be positioned between the support post 210 and the respective commissure tabs 220*a* and 220*b* (e.g., along an inner surface of the commissure tabs), while two layers of the support strip 230 may be provided on an opposing side of the respective commissure tabs 220*a* and 220*b* from the support post 210 (e.g., along an outer surface of the commissure tabs).

Additional, secondary sutures 260*a* and 260*b* may be used to secure the folded support strip to the commissure tabs as shown in FIG. 4. For example, the secondary sutures 260*a* and 260*b* may form a plurality of in-and-out stitches that are extended, each, in order (or in the reverse order): through respective first layers of the support strip 230, through respective second layers of the support strip 230, through respective commissure tabs 220*a* and 220*b* and through respective third layers of the support strip 230 in a radial direction. The secondary sutures may extend through the multiple layers of the support strip adjacent a respective reinforcing element that is positioned on that side of the support strip (e.g., around which the associated respective side of the support strip is wrapped). As shown in more detail in FIG. 5B, the in-and-out stitches of an example secondary suture 360*a* may form a suture line 362 that includes a plurality of apertures and/or markings in at least an outer layer of the support strip through which the secondary suture passes.

As used herein, the term "suture line" can also be referred to as a "stitch line." As further used herein in reference to the support strip, the term "aperture" refers to holes in the support strip used for stitching. In some examples, the holes are formed in the support strip while stitching and/or as a result of the stitching (e.g., the stitching formed by the secondary suture in the above example). In other examples, the holes may include pre-formed holes in the support strip that are made before stitching to provide a guide for the stitching that increases speed, integrity, and/or accuracy of assembly.

The pre-assembled commissure tab assembly, assembled as described in any of the examples above, may be attached to a corresponding commissure post, such as post 210 of FIG. 4 or post 310 of FIGS. 5A and 5B, or other commissure support structure of the frame. The commissure post can be a component of an actuator 80 of the prosthetic valve 10 shown in FIG. 1. For example, the upper portion of outer member 92 (FIG. 1) can serve as the commissure post 210 of FIG. 4 and/or post 310 of FIGS. 5A and 5B. In alternative embodiments, the prosthetic valve 10 can include commissure posts separate from the actuators. The separate commissure posts can be mounted to the inner surface of the frame 12, or can be integral portions of the frame, at locations circumferentially spaced from the actuators.

As shown in FIG. 4, the commissure tab assembly may be attached to the commissure post by extending a tertiary suture 270 across a first side of the commissure support post 210 between two opposing sides of the support strip 230, which are respectively disposed adjacent a second and third side of the commissure support post, the second and third sides being two circumferentially opposite sides of the commissure post 210. For example, the tertiary suture 270 may be used to form shoelace stitches around the post 210 and both ends of the suture 270 may be coupled together (e.g., forming a knot 278 at the top and/or bottom end). For illustrative clarity purposes, a tertiary suture and/or stitches formed by a tertiary suture is not shown with respect to the commissure assembly of FIGS. 5A and 5B, however, it is to be understood that stitches formed by a tertiary suture may be provided therein as described above with respect to FIG. 4 (e.g., passing between two sides of the support strip 330 across a side of the support post 310).

The pre-assembled commissure assembly may be further coupled to a support member of a frame of a prosthetic valve using additional reinforcing stitching, as will be described below. For example, the additional reinforcing stitching may be provided in addition to stitching that is formed using a tertiary suture (e.g., tertiary suture 270). For example, an additional reinforcing suture 266 may be extended around a larger region of the support strip (e.g., support strip 230 of FIG. 4) than the tertiary suture to form reinforcing stitching loops around a support post (e.g., support post 210). As shown in FIG. 4, the additional reinforcing suture 266 may wrap around a larger circumferential area of the commissure assembly (e.g., extending more than 270 degrees, or extending 360 degrees in some examples, around the support post 210 in the illustrated example) than the tertiary suture 270.

As further shown in FIG. 4, the additional reinforcing suture 266 passes through different layers of the commissure assembly components at a region of the commissure assembly that is opposite the first side of the commissure support post 210 (e.g., the side of the support post over which the tertiary suture 270 extends). For example, the additional reinforcing suture 266 may pass through, in order or in reverse order, one or more layers of the support strip 230 on a first side of the support strip, the first and second commissure tabs 220*a* and 220*b*, respectively, and one or more layers of the support strip 230 on a second side of the support strip opposite the first side. Ends of the additional reinforcing suture 266 may be tied together to form one or more knots 268 positioned along the first side of the support post 210.

As shown in FIG. 5A, an additional reinforcing suture 366 may form a plurality of reinforcing stitches (which may form one or more corresponding suture loops) crossing over a first (e.g., external) side of the support post 310, where at least one (e.g., each) stitch is secured using a respective knot 368 to tie ends of the additional reinforcing suture together. The illustrations in FIGS. 5A and 5B do not show tertiary sutures or associated stitching for clarity purposes, in order to show the additional reinforcing sutures more clearly. However, it is to be understood that the additional reinforcing suture 366 may be provided in addition to a tertiary suture that is used to form stitches across the support post 310 as described above with respect to tertiary suture 270 FIG. 4 in some examples.

In order to reduce the number of apertures in the support strip, and thereby increase the strength of the support strip (as each aperture may compromise the structural integrity of the support strip), the additional reinforcing suture 266 may pass through at least a portion of the apertures in one or more layers of the support strip through which the secondary sutures 260*a* and 260*b* pass through. In this way, the additional reinforcing suture 266 may at least partially pass through apertures included in the suture lines formed by the secondary sutures 260*a* and 260*b*. For example, as shown in FIG. 5B, the additional reinforcing suture 366 passes through multiple apertures in the secondary suture line 362. As shown, the suture loops extend substantially perpendicularly relative to the extension of the sutures forming stitches along the support strip in the secondary suture line 362. In this way, the secondary suture line 362 extends substantially perpendicularly (e.g., at between an 80-degree and a 100-degree angle) to the suture loops formed by the additional reinforcing suture 266.

In some examples, the additional reinforcing suture may include end portion extensions of one or more other sutures in the commissure assembly (e.g., end portion extensions of the secondary suture 260*a*/260*b* of FIG. 4 and/or secondary suture 360*a* of FIG. 5B). For example, end portion extensions of one or more sutures may be extended through the secondary suture line 362 and utilized to form additional suture loops around an external surface of the support strip 330 and the support post 310 (e.g., instead of being cut or directly tied off), pressing the support strip and/or adjacent commissure components onto the support post 310. The suture extension may be looped around the support strip and the support post (e.g., crossing over one another by extending in the directions indicated by the illustrated arrows on loops formed by the suture 366) to form a series of suture loops. For example, the suture loops may extend from a first region of an interior side of the support post 310 (e.g., a location of the suture line 362), around a first lateral side of the support post, across an external side of the support post, around a second lateral side of the support post, and to a second region of the interior side of the support post (e.g., a location of a suture line opposite the suture line 362, positioned on an opposite side of the support strip 330 from the suture line 362), where the internal side of the support post is opposite of the external side of the support post and the first and second lateral sides of the support post are opposite of one another and extend between the internal side of the support post and the external side of the support post. In this way, the suture loops and/or the stitches forming the suture loops may extend along at least three sides of the support post. In the illustrated example, the suture loops and/or the stitches forming the suture loops further extend along a portion of a remaining side of the support post, thus, the suture loops and/or stitches forming the suture loops extend more than 270 degrees around a circumference of the support post.

The suture loops may be stitched together at a respective end by a knot 368 or other coupling mechanism (e.g., adhesion, twisting, etc.). Such a configuration may be advantageous, as it may be formed in a reduced time and with reduced efforts relative to other securing mechanisms.

In an alternative approach, the suture extensions may be knotted together at each suture loop (or at a subset of the suture loops, such as every other suture loop, a top half of the suture loops, a bottom half of the suture loops, etc.). Such a configuration may provide improved tightness around the support post, as well as improved durability, relative to configurations with a single knot (or fewer knots), as a tear along one loop does not affect all of the remaining loops in the configuration with multiple knots.

Additional details regarding the assembly of the leaflets to the frame are disclosed in U.S. Application No. 62/985,558, filed Mar. 5, 2020, which is incorporated herein by reference.

Figure 6:
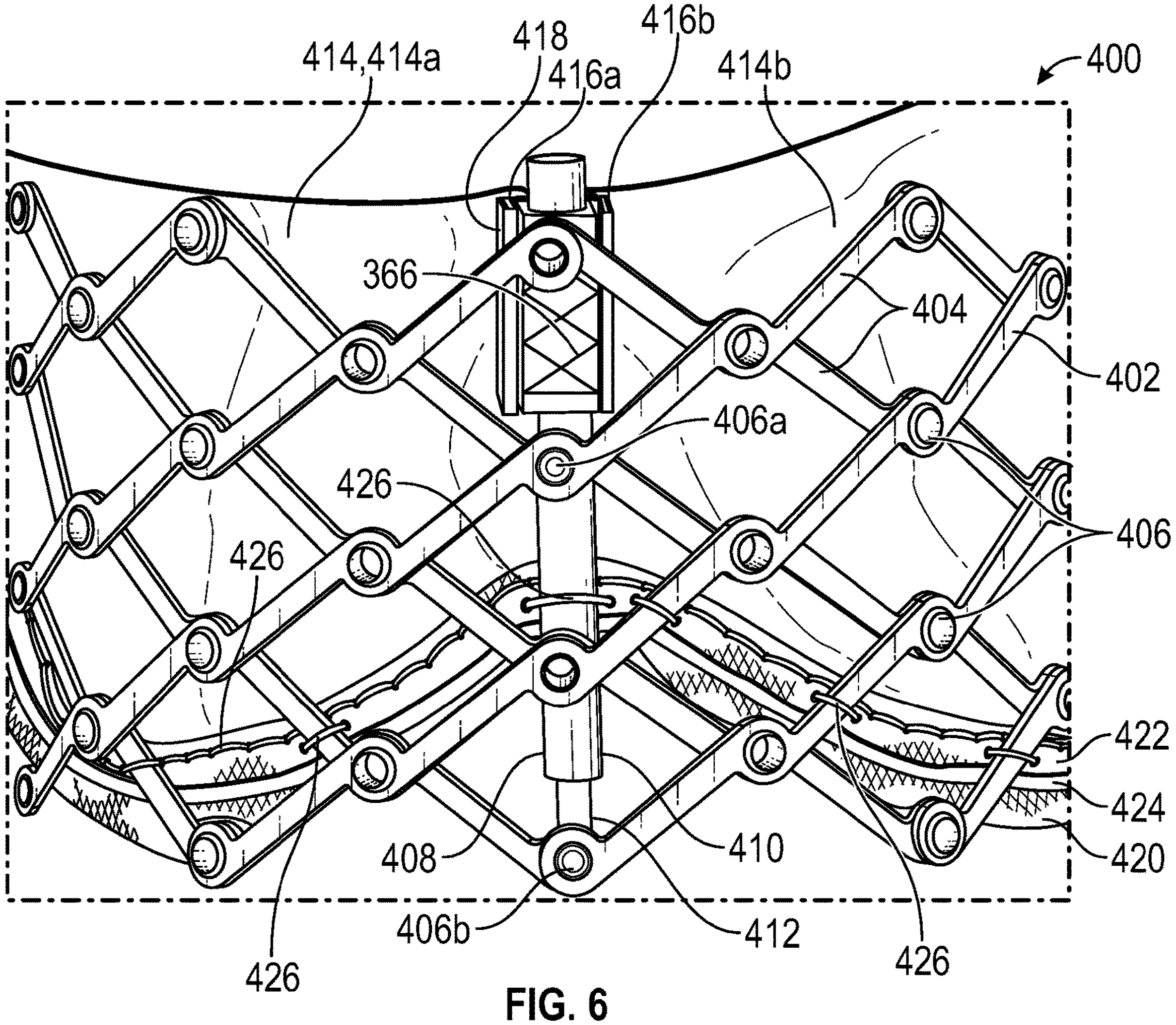
FIG. 6 is a side view of another embodiment of a prosthetic heart valve.

FIG. 6 shows a prosthetic heart valve 400, according to another embodiment. The prosthetic valve 400 comprises a frame 402 comprising a plurality of struts 404 pivotably connected to each other at a plurality of pivot joints 406. The frame 402 can have the same configuration as the frame 12 previously described. The frame 402 can further include a plurality of actuators 408, each of which can include an outer member 410 and an inner member 412. The outer member 410 can be pivotably coupled to a pivot joint of the frame, such as pivot joint 406*a*. The inner member 412 can be pivotably coupled to a pivot joint of the frame, such as pivot joint 406*b*. The actuators 408 can be push-pull type actuators wherein the outer member 410 and the inner member 412 are axially slidable relative to each other to effect radial compression and expansion of the frame 402. In alternative embodiments, the actuators 408 can be screw type actuators wherein one of the inner or outer members are rotatable relative to the other to effect radial compression and expansion of the frame 402. The actuators 408 can be any of the various actuators disclosed herein. The actuators 408 can also include locking mechanisms, as previously disclosed herein.

Figure 9:
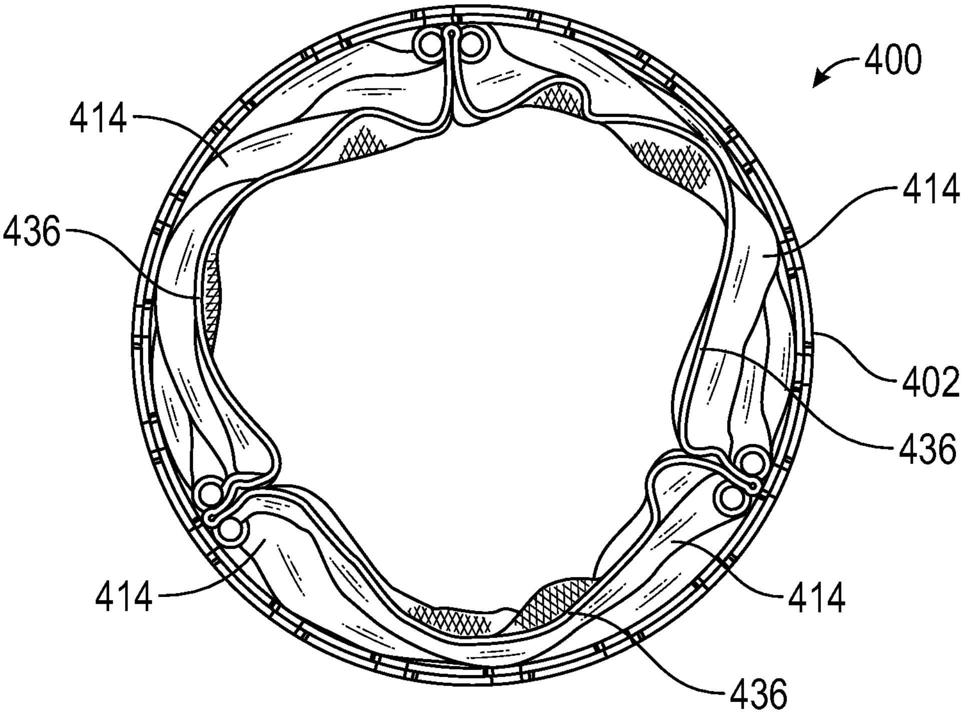
FIG. 9 is a top plan view of the prosthetic valve of FIG. 6, showing the leaflets in an open position.

The prosthetic valve 400 includes a valvular structure to regulate the flow of blood in one direction through the frame 402. The valvular structure can comprise one or more leaflets 414, including leaflets 414*a*, 414*b*. In particular embodiments, the prosthetic valve 400 has three leaflets, such as shown in FIG. 9. Adjacent leaflets 414 can be connected to each other to form commissures, which are connected to the frame. For example, as shown in FIG. 6, leaflets 414*a*, 414*b* can have commissure respective commissure tabs 416*a*, 416*b* that are connected to each other to form a commissure 418 connected to a corresponding outer member 410 of an actuator 408. In this manner, the outer member 410 functions as a commissure support post. Each leaflet 414 can be connected to two adjacent leaflets to form a plurality of commissures 418. Each commissure 418 can be connected to the commissure support post 410 using the technique shown in FIGS. 4, 5A, and 5B and can include a support member (e.g., support member 230 or 330) and reinforcing elements (e.g., reinforcing elements 232 or 332) as previously described. In other embodiments, the commissure 418 can be connected to a commissure support post that is separate from an actuator 408, or to one or more struts 404 of the frame.

In alternative embodiments, the commissures of the leaflets 414 can be formed and connected to the frame 402 using other techniques and mechanisms. For example, in some embodiments, pairs of commissure tabs can be connected to respective support members, such as clips or clamps, which in turn can be connected to respective commissure support posts. In other embodiments, pairs of commissures can be connected to selected struts 404 of the frame 402. Any of the various commissure attachment techniques and mechanisms disclosed in the following applications can be used to couple the commissures of the leaflet assembly to the frame 402: U.S. Publication Nos. 2018/0325665, 2019/0105153, and 2019/0192296, U.S. Patent Application Nos. 62/797,837, filed Jan. 28, 2019, 62/823,905, filed Mar. 26, 2019, 62/854,702, filed May 30, 2019, 62/928,993, filed Oct. 31, 2019, 62/959,723, filed Jan. 10, 2020, 62/971,011, filed Feb. 6, 2020, 62/985,558, filed Mar. 5, 2020, and 62/960,838, filed Jan. 14, 2020, and PCT Application Nos. PCT/US2019/61392, filed Nov. 14, 2019, PCT/US2020/18664, filed Feb. 18, 2020, all of which are incorporated herein by reference in their entireties.

In particular embodiments, each leaflet 414 has the same configuration as the leaflet 100 of FIG. 3. However, in alternative embodiments, the leaflets 414 can have various other configurations, including as of those disclosed herein (e.g., leaflet 500 or leaflet 500', described below).

The prosthetic valve 400 can have one or more skirts or reinforcing members to connect the cusp edge portions of the leaflets 414 to the frame 402. As shown in FIG. 6, for example, the prosthetic valve 400 includes first and second reinforcing members 420, 422, respectively, (also referred to as reinforcing strips 420, 422) positioned on opposite sides of the cusp edge portions 424 of the leaflets 414. The first reinforcing member 420 is positioned against the inner surfaces of the cusp edge portions 424 and the second reinforcing member 422 is positioned against the outer surfaces of the cusp edge portions 424. In this manner, the cusp edge portions 424 are sandwiched between the first and second reinforcing members 420, 422. The cusp edge portions 424 can be connected to the first and second reinforcing members 420, 422 with sutures, such as a scalloped suture line 426, which can be formed by a plurality of in-and-out stitches that extend through the first and second reinforcing members 420, 422 and the cusp edge portions 424. As further shown in FIG. 6, the first reinforcing member 420 can have an inflow edge portion that extends below the inflow edge of the leaflets 414 and the second reinforcing member 422 toward the inflow end of the frame.

Figure 8:
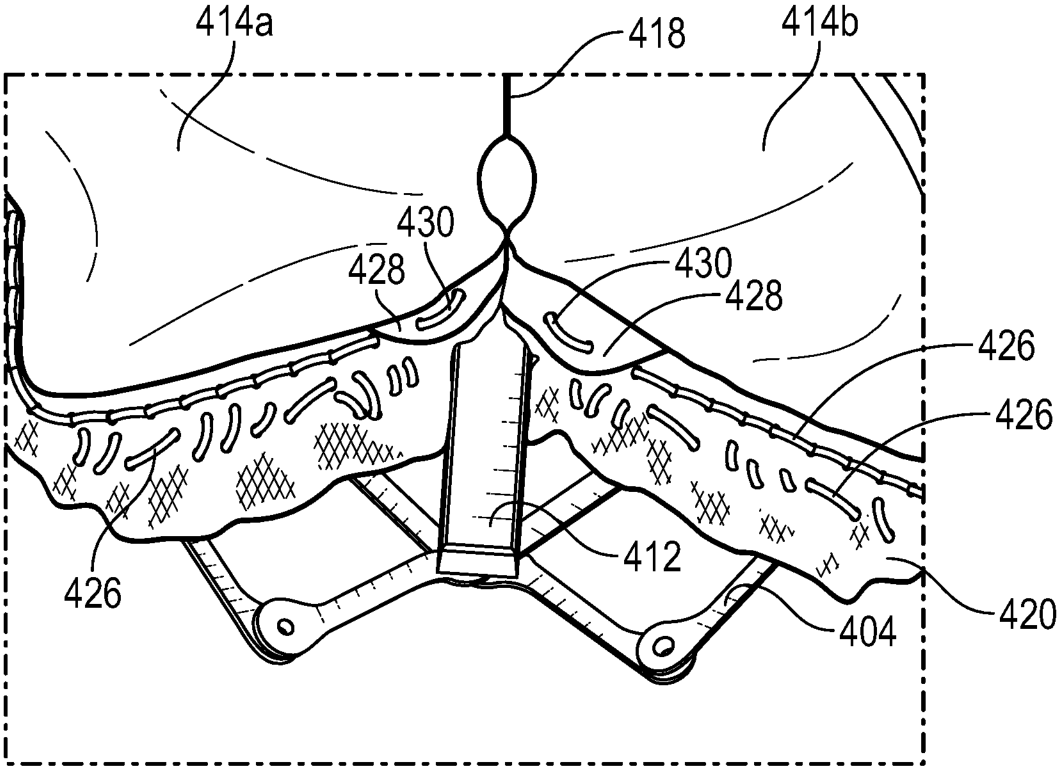
FIG. 8 is a perspective view of a portion of the prosthetic valve of FIG. 6, showing the inside the prosthetic valve.

The assembly of the leaflets 414 and the first and second reinforcing members 420, 422 can be secured to the frame, such as with a plurality of sutures 426. Each suture 426 can extend through one or more layers of the reinforcing members 420, 422 and the leaflets and around a strut 404 or a component of an actuator 408 (such as an outer member 410). As shown in FIG. 8, the first reinforcing member 420 can include a pair of upper wings members 428 positioned below each commissure 418. The wing members 428 can be folded downwardly against the main portion of the reinforcing member 420 and can be secured in place with sutures 430.

Figure 7:
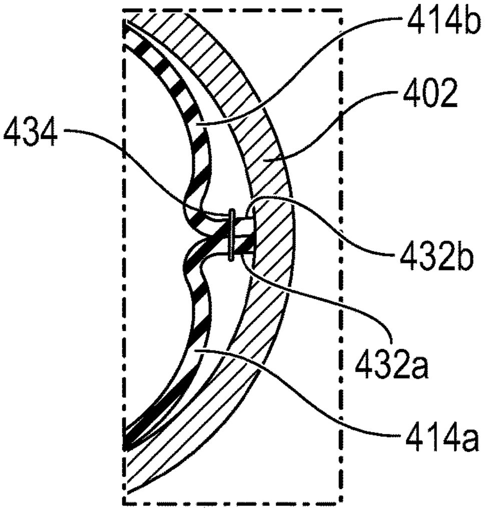
FIG. 7 is a cross-sectional view of a portion of the prosthetic valve of FIG. 6 showing a pair of sub-commissure tabs of two adjacent leaflets extending radially outwardly toward an inner surface of the frame of the prosthetic valve.

Referring to FIGS. 7 and 8, each leaflet 414*a*, 414*b* can include a sub-commissure portion 432*a*, 432*b*, respectively (which can also be referred to as sub-commissure tabs 432*a*, 432*b*), similar to sub-commissure tabs 142 (FIG. 3). In the embodiment of FIGS. 7 and 8, the sub-commissure portions 432*a*, 432*b* are folded relative to the cusp edge portions 424 and extend radially outwardly toward the frame 402. The sub-commissure portions 432*a*, 432*b* can be connected to each other, such as with a suture 434. In particular embodiments, the sub-commissure portions 432*a*, 432*b* are not fixed or directly connected to the frame (e.g., there are no sutures extending through the sub-commissure portions 432*a*, 432*b* and around any components of the frame). The leaflets 414*a*, 416*b* can have sub-commissure edges (similar to sub-commissure edges 116, 118 of FIG. 3) between the commissure tabs 416*a*, 416*b* and the sub-commissure tabs 432*a*, 432*b* that are not fixed or directly connected to the frame, which allows the leaflets to stretch to some degree along the sub-commissure edges when the prosthetic valve is radially compressed to the radially compressed state for delivery into a patient's body.

The first and second reinforcing members 420, 422 can be formed from any of various suitable biocompatible materials, including any of various synthetic materials (e.g., polyethylene terephthalate (PET)) or natural tissue (e.g., pericardial tissue).

In particular embodiments, a leaflet assembly comprising the leaflets 414 and the first and second reinforcing members 420, 422 can be pre-assembled prior to mounting these components to the frame 402. For example, the pre-assembled leaflet assembly can include the first and second reinforcing members 420, 422 sutured to the cusp edge portions 424 of the leaflets 414. Once formed, the leaflet assembly can be positioned inside of the frame 402 and the commissures 418 and the cusp edge portions 424 can be secured to the frame 402 as described above.

In particular embodiments, each of the first and second reinforcing members 420, 422 can be a unitary or continuous piece of material. In alternative embodiments, one or both of the reinforcing members 420, 422 can comprise a plurality of discrete pieces of material, each of which is secured to the cusp edge portion 424 of a corresponding leaflet 414. For example, if three leaflets 414 are provided, the first reinforcing member 420 can comprise three discrete sections, each of which is secured to the cusp edge portion 424 of a corresponding leaflet 414. Similarly, the second reinforcing member 422 can comprise three discrete sections, each of which is secured to the cusp edge portion 424 of a corresponding leaflet 414.

In alternative embodiments, one or both of the reinforcing members 420, 422 can comprise a wider skirt (such as skirt 20 of FIG. 1), which can be sized to cover a plurality of the cells or openings between the struts 404 of the frame and therefore can function to inhibit paravalvular leakage between the prosthetic valve and the surrounding tissue once implanted. Additionally, the prosthetic valve 400 can also include an outer skirt positioned around the outside of the frame 402 (such as outer skirt 450 shown in FIG. 11).

It has been found that the orientation of the sub-commissure tabs 432*a*, 432*b* can affect the ability of the leaflets 414 to fully open under the forward flow of blood (e.g., during systole for a prosthetic aortic valve). In particular, it has been found that the leaflets 414 may not fully open when the sub-commissure tabs 432*a*, 432*b* extend radially outwardly toward the frame 402, as shown in FIGS. 7 and 8.

Figure 10:
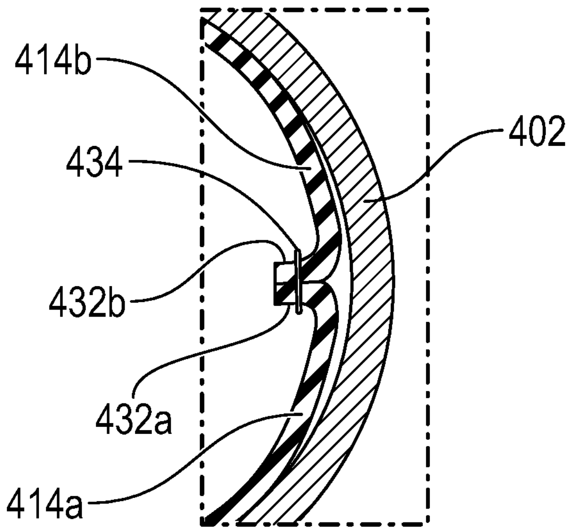
FIG. 10 is a cross-sectional view similar to FIG. 7 wherein the pair of sub-commissure tabs of two adjacent leaflets extend radially inwardly away from the frame.
Figure 11:
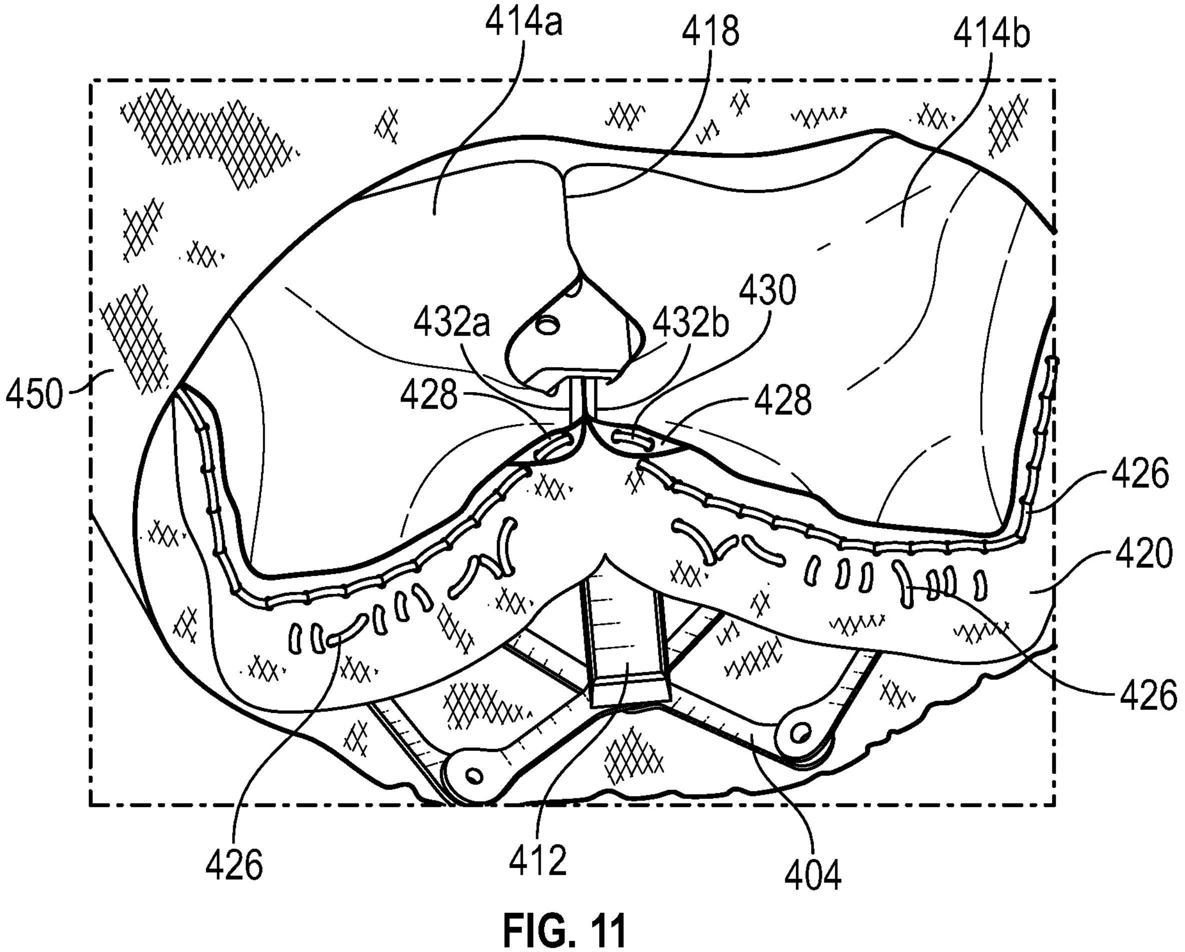
FIG. 11 is a perspective view of a prosthetic valve similar to FIG. 8 wherein the prosthetic valve includes sub-commissure tabs extending radially inwardly in the manner shown in FIG. 10.

FIGS. 10 and 11 show an alternative orientation for the sub-commissure tabs 432*a*, 432*b* of the prosthetic valve 400. In this embodiment, the sub-commissure tabs 432*a*, 432*b* are folded relative to the cusp edge portions 424 and extend radially inwardly away the frame 402 and toward the center of the lumen of the prosthetic valve. In particular embodiments, the sub-commissure portions 432*a*, 432*b* are not fixed or directly connected to the frame (e.g., there are no sutures extending through the sub-commissure portions 432*a*, 432*b* and around any components of the frame). It has been found that the leaflets 414 can open to a greater extent under the forward flow of blood when the sub-commissure tabs 432*a*, 432*b* extend radially inwardly as compared to when the sub-commissure tabs 432*a*, 432*b* extend radially outwardly.

Figure 12:
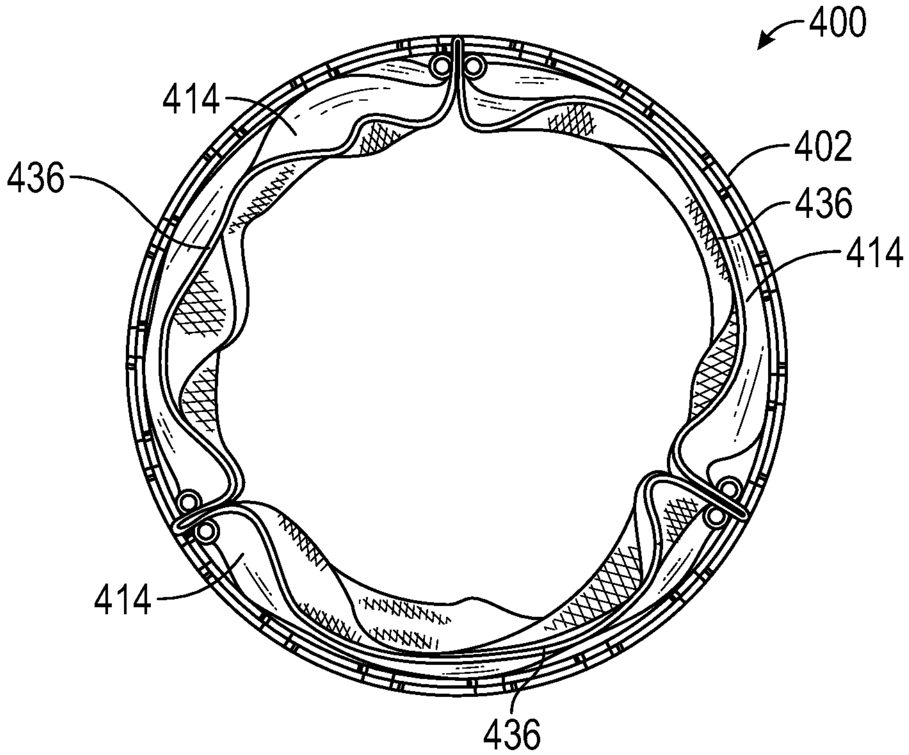
FIG. 12 is a top plan view of the prosthetic valve of FIG. 11, showing the leaflets in an open position.

FIG. 9 is a top plan view of the prosthetic valve 400 having the sub-commissure tabs 432*a*, 432*b* oriented radially outwardly and the leaflets 414 in the open position under the forward flow of blood. FIG. 12 is a top plan view of the prosthetic valve 400 having the sub-commissure tabs 432*a*, 432*b* oriented radially inwardly and the leaflets 414 in the open position under the forward flow of blood. Comparing FIG. 9 and FIG. 12, it can be seen that a greater extent of the free edges 436 (the outflow edges) of the leaflets 414 open wider (closer to the frame) in FIG. 12 than in FIG. 9. Advantageously, orienting the sub-commissure tabs in the inward direction therefore can increase the effective outflow orifice of the prosthetic valve, thereby improving the hemodynamics of the prosthetic valve.

Figure 13:
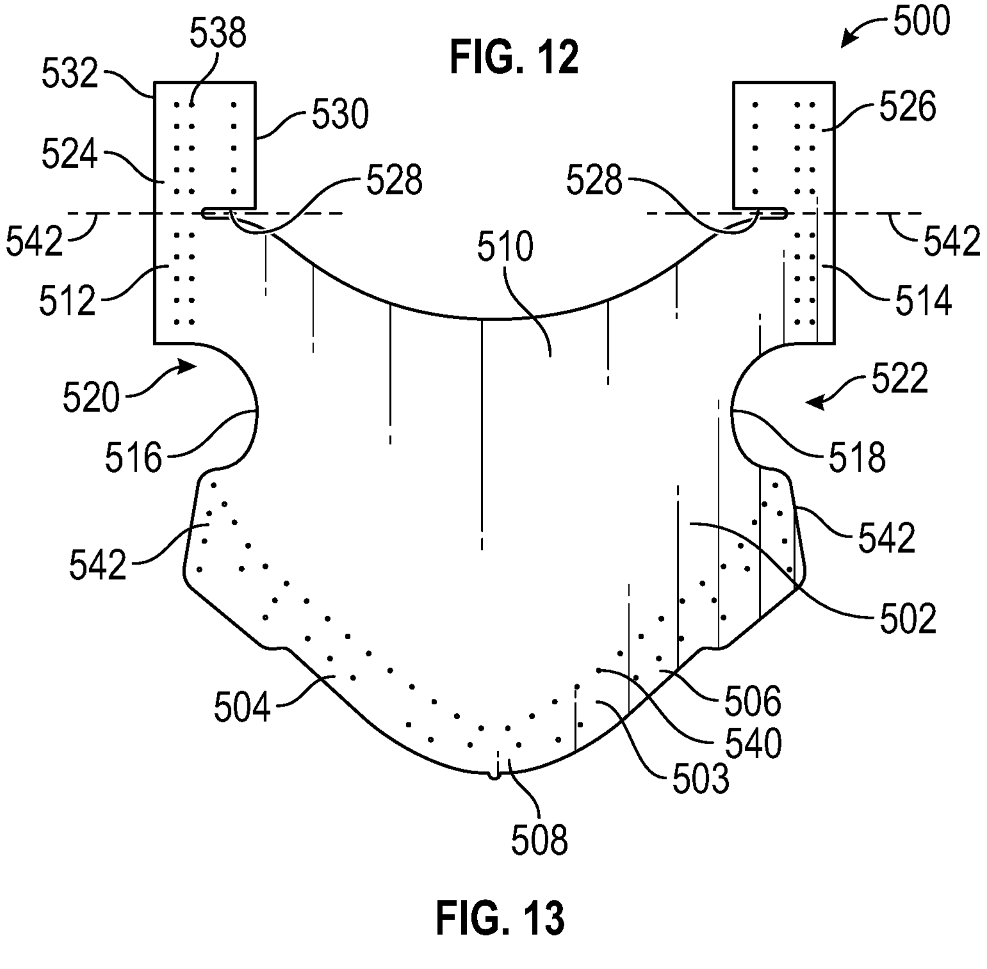
FIG. 13 is a flattened view of a leaflet for a prosthetic heart valve, according to another embodiment.

FIG. 13 shows a leaflet 500 for a prosthetic heart valve, according to another embodiment. Any of the prosthetic heart valves disclosed herein (e.g., any of the embodiments of FIGS. 1-12) can include a valvular structure comprising one or more of the leaflets 500 assembled within a frame of a prosthetic heart valve. The leaflet 500 is similar to leaflet 100 of FIG. 3 and includes many of the same features.

The leaflet 100 can comprise a main body 502 with a cusp (e.g., inflow) edge portion 503 including a first (left) side cusp edge portion 504 and a second (right) side cusp edge portion 506 which connect together at an inflow-most end portion 508 of the leaflet 500. The upper end portions of the cusp edge portions 504, 506 can form sub-commissure tabs 542. The leaflet 500 can include commissure tabs 512 and 514, extending from opposite sides of the main body 502. An outflow edge portion 510 (also referred to as a coaptation edge portion) extends across the leaflet 500, between the commissure tabs 512 and 514. A curved edge portion 516, 518 extends between and connects a corresponding one of the commissure tabs 512 and 514 and a corresponding one of the first and second cusp edge portions 504 and 506. Each curved edge portion 516, 518 defines an open region on either side of the leaflet 500, referred to herein as a notch or window 520, 522.

The leaflet 500 can include upper tabs 524, 526 extending upwardly from commissure tabs 512, 514, respectively. The leaflet 500 can include notches 528 between the upper tabs 524, 526 and the commissure tabs 512, 514. Each notch 528 can extend from an inner edge 530 of a corresponding upper tab 524, 526 to a location between the inner and outer edges 530, 532 of the upper tab. In this manner, each upper tab 524, 526 is connected to a corresponding commissure tab 512, 514 for only part of the width the upper tab, so as to facilitate folding of the upper tabs against the commissure tabs during assembly of the leaflet assembly. In other embodiments, the leaflet 500 can be formed without notches 528 such that each upper tab is connected to a commissure tab along the entire width of the upper tab.

In some embodiments, the commissure tabs 512 and 514 and the upper tabs 524, 526 can include a plurality of columns or lines of apertures 538, adapted to receive lines of fasteners (e.g., sutures) during folding and securing of the commissure tabs to form commissures (as previously described above with reference to FIGS. 4, 5A and 5B). As further shown in FIG. 13, in some embodiments, each of the first and second edge portions 504 and 506 can include one or more lines of apertures 540 adapted to receive fasteners (e.g., sutures) which secures the first and second cusp edge portions 504 and 506 to one or more skirts or reinforcing members (e.g., reinforcing members 420, 422) that is configured to be attached to the frame of the prosthetic heart valve.

In particular embodiments, a leaflet assembly comprising a plurality of leaflets 500 can be formed. In forming the leaflet assembly, the upper tabs 524, 526 can be folded downwardly against the commissure tabs 512, 514 along horizontal fold lines 542. Each upper tab 524, 526 can be secured to a corresponding commissure tab 512, 514, such as with sutures. A support strip (e.g., support strip 230 or 330) can be sutured to each pair of commissure tabs, as previously described. One or more skirts or reinforcing members (e.g., reinforcing members 420, 422) can be sutured to the cusp edge portions of the leaflets, as previously described. Each sub-commissure tab 542 can be sutured to an adjacent sub-commissure tab 542 of an adjacent leaflet, such as shown in FIG. 7 or FIG. 10. The leaflet assembly can be mounted to a frame of a prosthetic heart valve as previously described. For example, each commissure can be secured to a commissure support post (e.g., such as a component of an actuator), as previously described in connection with FIGS. 4, 5A and 5B, or using other techniques or mechanisms previously decsribed. The cusp edge portions of the leaflets and any skirts or reinforcing members can be connected to the frame, as previously described in connection with FIG. 6.

Figure 14:
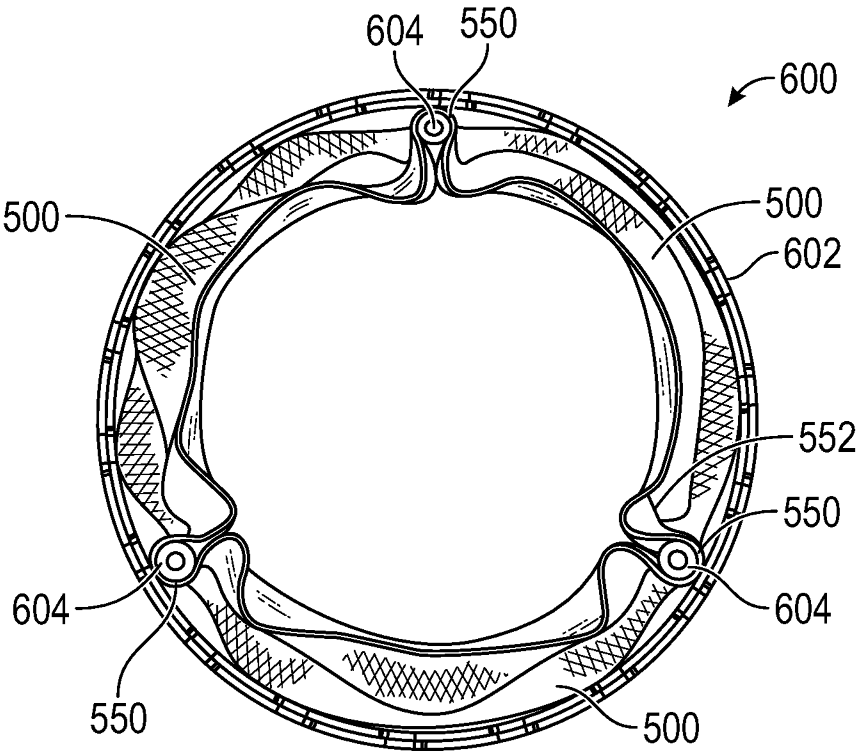
FIG. 14 is a top plan view of a prosthetic heart valve that includes leaflets of the type shown in FIG. 13.

FIG. 14 shows a top plan view of an exemplary prosthetic heart valve 600 comprising a frame 602 and three leaflets 500 mounted to the frame 602. The frame 602 can have the same configuration as frame 12 or frame 402 and therefore is not further described. The leaflet assembly includes commissures 550 mounted to respective commissure posts 604 (which can be components of actuators).

When the prosthetic valve is radially expanded from a compressed (delivery) state, a small amount of slack can form along sub-commissure edge portions 516, 518, depending on the height and/or width of the windows 520, 522. As depicted in FIG. 14, small folds 552 can form along the sub-commissure edge portions 516, 518. During cyclic operation of the prosthetic valve 600, these folds 552 can transition between an open state under the forward flow of blood (e.g., during systole for a prosthetic aortic valve) and a closed state under the reverse flow of blood (e.g., during diastole for a prosthetic aortic valve). In the open state, the folds may contact the inner surface of the frame, which can cause abrasion of the leaflets, and may limit the extent that the leaflets 500 can fully open under the forward flow of blood.

Figure 15:
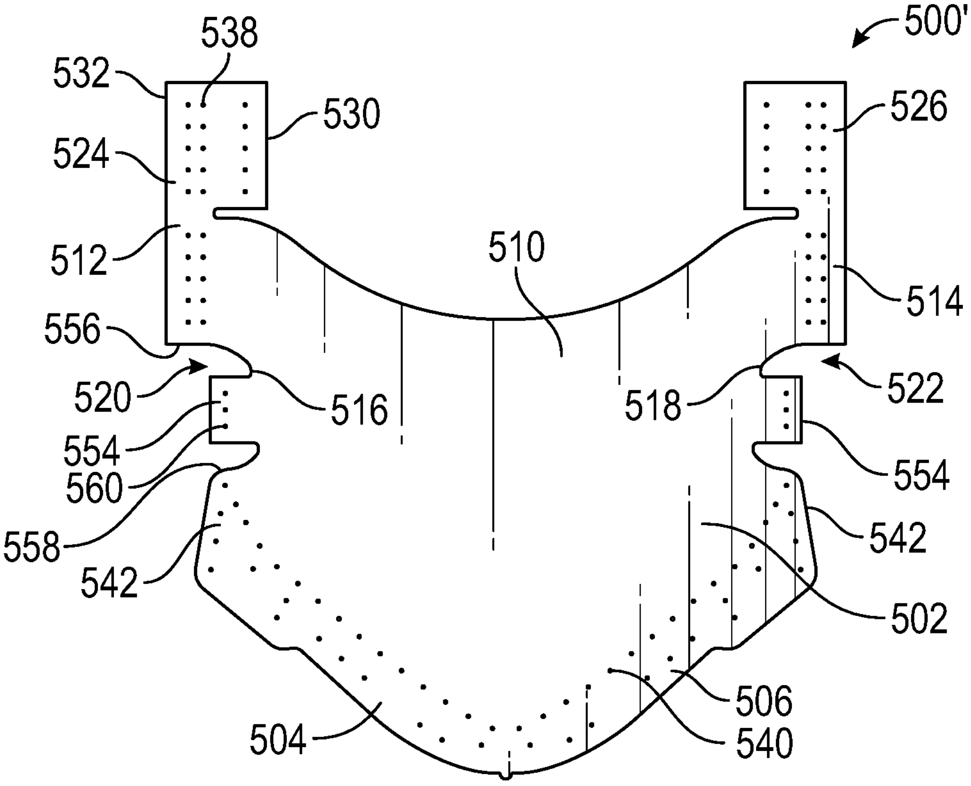
FIG. 15 is a flattened view of a leaflet for a prosthetic heart valve, according to another embodiment.

FIG. 15 shows an exemplary leaflet 500' for a prosthetic heart valve that can prevent or at least minimize the formation of folds 552 during operation of the prosthetic valve. Any of the prosthetic heart valves disclosed herein (e.g., any of the embodiments of FIGS. 1-12) can include a valvular structure comprising one or more of the leaflets 500 assembled within a frame of a prosthetic heart valve. The components of the leaflet 500 that are present in the leaflet 500' are given the same reference numbers and therefore are not further described.

Unlike leaflet 500, the leaflet 500' includes additional sub-commissure tabs 554 extending laterally from the sub-commissure edge portions 516, 518 within the windows 520, 522. The sub-commissure tabs 554 can be referred to as upper sub-commissure tabs 554 while the sub-commissure tabs 542 can be referred to as lower sub-commissure tabs 542. Each sub-commissure tab 554 can be spaced from a lower edge 556 of a corresponding commissure tab 512, 514 and an upper edge 558 of a corresponding tab 542. In certain embodiments, each sub-commissure tab 554 can be positioned equidistant from the edges 556 and 558. Each sub-commissure tab 554 can be formed with one or more lines of apertures 560 for receiving sutures.

A leaflet assembly comprising a plurality of leaflets 500' can be formed in the same manner as described above for the leaflet 500. Additionally, each sub-commissure tab 554 can be connected to an adjacent sub-commissure tab 554 of an adjacent leaflet, such as with sutures (which can extend through apertures 560). In some embodiments, the sub-commissure tabs 554 can be folded inwardly relative to the edge portions 516, 518 such that when assembled to a frame, each pair of connected sub-commissure tabs 554 extends radially inwardly toward the center of the prosthetic valve (similar to the tabs 432*a*, 432*b* of FIG. 10). In alternative embodiments, each pair of connected sub-commissure tabs 554 can be folded outwardly relative to the edge portions 516, 518 such that when assembled to a frame, each pair of connected sub-commissure tabs 554 extends radially outwardly toward the frame (similar to the tabs 432*a*, 432*b* of FIG. 7).

By connecting the sub-commissure tabs 554 to each other, the formation of folds along the edge portions 516, 518 can be prevented or minimized. Advantageously, this can prevent or minimize contact of the leaflets with the frame, thereby preventing or minimizing leaflet abrasion, and can promote full opening of the leaflets under the forward flow of blood to maximize the effective outflow orifice of the valve and to reduce the pressure gradient across the valve under the forward flow of blood. As described above in connection with FIG. 10, folding the lower sub-commissure tabs 542 inwardly (like tabs 432*a*, 432*b* in FIG. 10) can promote opening of the leaflets under the forward flow of blood. Thus, in some embodiments, both the lower sub-commissure tabs 442 and the upper sub-commissure tabs 554 are folded inwardly to further promote opening of the leaflets under the forward flow of blood.

The width of the sub-commissure tabs 554 (in the horizontal direction in FIG. 15) can be selected to permit each tab to be connected to an adjacent tab 554 of an adjacent leaflet. The height of each tab 554 (in the vertical direction in FIG. 15) can be selected to optimize performance of the leaflets, and in particularly, prevent or minimize fold formation and movement of the tabs relative to the frame, thereby mitigating abrasion and promoting leaflet opening under the forward flow of blood. In particular embodiments, the width of the tabs 554 is about 2 mm or greater and the height of the tabs is about 2 mm or greater.

The sub-commissure tabs 554 can be incorporated into leaflets having other overall shapes or configurations that are different than that shown in FIG. 15. For example, in one implementation, a leaflet 100 (shown in FIG. 3) can include sub-commissure tabs 554 extending laterally from edge portions 116, 118. In other embodiments, any of the leaflets disclosed in U.S. Publication No. 2018/0028310, which is incorporated herein by reference, can include sub-commissure tabs 554.

Although the present disclosure is described in the context of mechanically expandable heart valves, any of the leaflets, leaflet assemblies and valve assembly methods disclosed herein can be applied to other types of prosthetic heart valves, such as plastically-expandable (e.g., balloon expandable) heart valves or self-expandable heart valves. Thus, any of the leaflets, leaflet assemblies and assembly methods can be used to assemble a prosthetic valve comprising a frame made of a plastically-expandable material (e.g., stainless steel, a cobalt chromium alloy, etc.) or a shape memory, self-expanding material (e.g., a nickel titanium alloy (NiTi), such as nitinol) as known in the art. When constructed of a plastically-expandable material, the frame (and thus the prosthetic valve) can be crimped to a radially collapsed configuration on a delivery catheter and then expanded inside a patient by an inflatable balloon or equivalent expansion mechanism. When constructed of a self-expandable material, the frame (and thus the prosthetic valve) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size. Examples of prosthetic heart valves that have plastically-expandable frames are disclosed in U.S. Pat. No. 9,393,110 and U.S. Publication No. 2018/0028310. Examples of prosthetic heart valves that have self-expandable frames are disclosed in U.S. Pat. No. 8,652,202 and Publication No. 2016/0317301, which are incorporated herein by reference.

Figure 16:
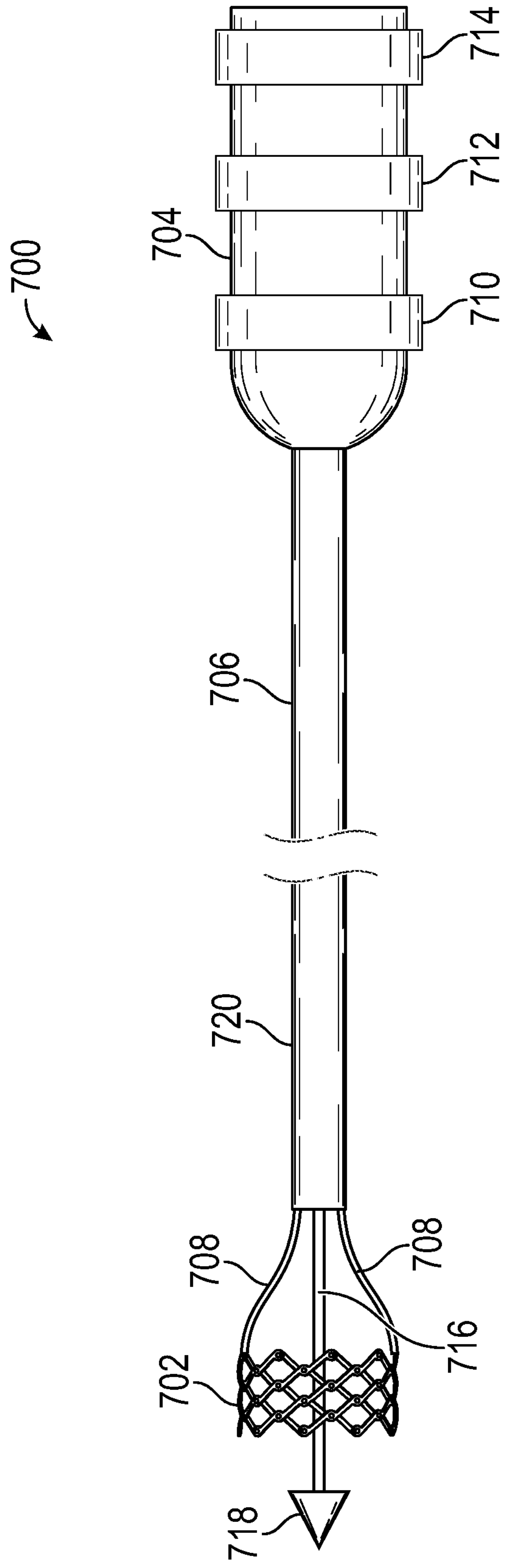
FIG. 16 is a side elevation view of a delivery apparatus for a prosthetic heart valve, according to one example.

FIG. 16 illustrates a delivery apparatus 700, according to one example, adapted to deliver a prosthetic heart valve 702 (e.g., valve 10, 400, 600). The prosthetic valve 702 can be releasably coupled to the delivery apparatus 700. It should be understood that the delivery apparatus 700 and other delivery apparatuses disclosed herein can be used to implant prosthetic devices other than prosthetic valves, such as stents or grafts.

The delivery apparatus 700 in the illustrated embodiment generally includes a handle 704, a first elongated shaft 706 (which comprises an outer shaft in the illustrated example) extending distally from the handle 704, at least one actuator assembly 708 extending distally from the handle through the outer shaft 706, and a second elongated shaft 716 (which comprises an inner shaft in the illustrated example) extending distally from the handle through the outer shaft 706. The at least one actuator assembly 708 can be configured to radially expand and/or radially collapse the prosthetic valve 702 when actuated. A nosecone 718 can be mounted to the distal end of the second shaft 716. The second shaft 716 and the nosecone 718 can define a guidewire lumen sized for receiving a guidewire so that the delivery apparatus can be advanced over a guidewire previously inserted into a patient's body.

Though the illustrated embodiment shows two actuator assemblies 708 for purposes of illustration, it should be understood that one actuator 708 can be provided for each actuator on the prosthetic valve. For example, three actuator assemblies 708 can be provided for a prosthetic valve having three actuators. In other embodiments, a greater or fewer number of actuator assemblies can be present.

In some embodiments, a distal end portion 720 of the shaft 706 can be sized to house the prosthetic valve in its radially compressed, delivery state during delivery of the prosthetic valve through the patient's vasculature. In this manner, the distal end portion 720 functions as a delivery sheath or capsule for the prosthetic valve during delivery, The actuator assemblies 708 can be releasably coupled to the prosthetic valve 702. For example, in the illustrated embodiment, each actuator assembly 708 can be coupled to a respective actuator of the prosthetic valve 702. Each actuator assembly 708 can comprise a support tube, an actuator member, and optionally a locking tool. When actuated, the actuator assembly can transmit pushing and/or pulling forces to portions of the prosthetic valve to radially expand and collapse the prosthetic valve as previously described. The actuator assemblies 708 can be at least partially disposed radially within, and extend axially through, one or more lumens of the outer shaft 706. For example, the actuator assemblies 708 can extend through a central lumen of the shaft 706 or through separate respective lumens formed in the shaft 706.

The handle 704 of the delivery apparatus 700 can include one or more control mechanisms (e.g., knobs or other actuating mechanisms) for controlling different components of the delivery apparatus 700 in order to expand and/or deploy the prosthetic valve 702. For example, in the illustrated embodiment the handle 704 comprises first, second, and third knobs 710, 712, and 714.

The first knob 710 can be a rotatable knob configured to produce axial movement of the outer shaft 706 relative to the prosthetic valve 702 in the distal and/or proximal directions in order to deploy the prosthetic valve from the delivery sheath 720 once the prosthetic valve has been advanced to a location at or adjacent the desired implantation location with the patient's body. For example, rotation of the first knob 710 in a first direction (e.g., clockwise) can retract the sheath 720 proximally relative to the prosthetic valve 702 and rotation of the first knob 710 in a second direction (e.g., counter-clockwise) can advance the sheath 720 distally. In other embodiments, the first knob 710 can be actuated by sliding or moving the knob 710 axially, such as pulling and/or pushing the knob. In other embodiments, actuation of the first knob 710 (rotation or sliding movement of the knob 710) can produce axial movement of the actuator assemblies 708 (and therefore the prosthetic valve 702) relative to the delivery sheath 720 to advance the prosthetic valve distally from the sheath 720.

The second knob 712 can be a rotatable knob configured to produce radial expansion and/or contraction of the prosthetic valve 702. For example, rotation of the second knob 712 can move the actuator member and the support tube axially relative to one another. Rotation of the second knob 712 in a first direction (e.g., clockwise) can radially expand the prosthetic valve 702 and rotation of the second knob 712 in a second direction (e.g., counter-clockwise) can radially collapse the prosthetic valve 702. In other embodiments, the second knob 712 can be actuated by sliding or moving the knob 712 axially, such as pulling and/or pushing the knob.

The third knob 714 can be a rotatable knob configured to retain the prosthetic heart valve 102 in its expanded configuration. For example, the third knob 714 can be operatively connected to a proximal end portion of the locking tool of each actuator assembly 708. Rotation of the third knob in a first direction (e.g., clockwise) can rotate each locking tool to advance the locking nuts to their distal positions to resist radial compression of the frame of the prosthetic valve, as described above. Rotation of the knob 714 in the opposite direction (e.g., counterclockwise) can rotate each locking tool in the opposite direction to decouple each locking tool from the prosthetic valve 702. In other embodiments, the third knob 714 can be actuated by sliding or moving the third knob 714 axially, such as pulling and/or pushing the knob.

Although not shown, the handle 704 can include a fourth rotatable knob operative connected to a proximal end portion of each actuator member. The fourth knob can be configured to rotate each actuator member, upon rotation of the knob, to unscrew each actuator member from the proximal portion of a respective actuator. As described above, once the locking tools and the actuator members are uncoupled from the prosthetic valve 702, they can be removed from the patient.

Delivery Techniques

For implanting a prosthetic valve within the native aortic valve via a transfemoral delivery approach, the prosthetic valve is mounted in a radially compressed state along the distal end portion of a delivery apparatus. The prosthetic valve and the distal end portion of the delivery apparatus are inserted into a femoral artery and are advanced into and through the descending aorta, around the aortic arch, and through the ascending aorta. The prosthetic valve is positioned within the native aortic valve and radially expanded (e.g., by inflating a balloon, actuating one or more actuators of the delivery apparatus, or deploying the prosthetic valve from a sheath to allow the prosthetic valve to self-expand). Alternatively, a prosthetic valve can be implanted within the native aortic valve in a transapical procedure, whereby the prosthetic valve (on the distal end portion of the delivery apparatus) is introduced into the left ventricle through a surgical opening in the chest and the apex of the heart and the prosthetic valve is positioned within the native aortic valve. Alternatively, in a transaortic procedure, a prosthetic valve (on the distal end portion of the delivery apparatus) are introduced into the aorta through a surgical incision in the ascending aorta, such as through a partial J-sternotomy or right parasternal mini-thoracotomy, and then advanced through the ascending aorta toward the native aortic valve.

For implanting a prosthetic valve within the native mitral valve via a transseptal delivery approach, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, into the right atrium, across the atrial septum (through a puncture made in the atrial septum), into the left atrium, and toward the native mitral valve. Alternatively, a prosthetic valve can be implanted within the native mitral valve in a transapical procedure, whereby the prosthetic valve (on the distal end portion of the delivery apparatus) is introduced into the left ventricle through a surgical opening in the chest and the apex of the heart and the prosthetic valve is positioned within the native mitral valve.

For implanting a prosthetic valve within the native tricuspid valve, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, and into the right atrium, and the prosthetic valve is positioned within the native tricuspid valve. A similar approach can be used for implanting the prosthetic valve within the native pulmonary valve or the pulmonary artery, except that the prosthetic valve is advanced through the native tricuspid valve into the right ventricle and toward the pulmonary valve/pulmonary artery.

Another delivery approach is a transatrial approach whereby a prosthetic valve (on the distal end portion of the delivery apparatus) is inserted through an incision in the chest and an incision made through an atrial wall (of the right or left atrium) for accessing any of the native heart valves. Atrial delivery can also be made intravascularly, such as from a pulmonary vein. Still another delivery approach is a transventricular approach whereby a prosthetic valve (on the distal end portion of the delivery apparatus) is inserted through an incision in the chest and an incision made through the wall of the right ventricle (typically at or near the base of the heart) for implanting the prosthetic valve within the native tricuspid valve, the native pulmonary valve, or the pulmonary artery.

In all delivery approaches, the delivery apparatus can be advanced over a guidewire and/or an introducer sheath previously inserted into a patient's vasculature. Moreover, the disclosed delivery approaches are not intended to be limited. Any of the prosthetic valves disclosed herein can be implanted using any of various delivery procedures and delivery devices known in the art.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic heart valve comprising: an annular frame comprising a plurality of interconnected struts, wherein the frame is radially compressible and expandable between a radially compressed state and a radially expanded state; and a plurality of leaflets situated within the frame, each leaflet comprising a main body, two opposing commissure tabs arranged on opposite sides of the main body and two opposing sub-commissure tabs arranged on opposite sides of the main body; wherein each commissure tab of a leaflet is paired with an adjacent commissure tab of an adjacent leaflet to form a commissure that is coupled to the frame; wherein each sub-commissure tab is paired with an adjacent sub-commissure tab of an adjacent leaflet and connected thereto, wherein each pair of sub-commissure tabs extends radially inwardly relative to the frame.

Example 2. The prosthetic heart valve of any example herein, particularly example 1, wherein the sub-commissure tabs of each pair of sub-commissure tabs are sutured to each other.

Example 3. The prosthetic heart valve of any example herein, particularly any of examples 1-2, wherein each leaflet has a cusp edge portion extending from one sub-commissure tab to the other sub-commissure tab of the leaflet, wherein the cusp edge portion is coupled to the frame.

Example 4. The prosthetic heart valve of any example herein, particularly example 3, further comprising a first reinforcing member sutured to the cusp edge portions of the leaflets and to selected struts of the frame.

Example 5. The prosthetic heart valve of any example herein, particularly example 4, further comprising a second reinforcement member sutured to the cusp edge portions of the leaflets, wherein the first and second reinforcing members are positioned on opposite sides of the cusp edge portions of the leaflets.

Example 6. The prosthetic heart valve of any example herein, particularly any of examples 1-5, wherein the pairs of sub-commissure tabs are not directly connected to the frame.

Example 7. The prosthetic heart valve of any example herein, particularly any of examples 1-6, wherein the main body of each leaflet is formed with pair of notches, each of which extends between a commissure tab and a sub-commissure tab, wherein the notches are not directly connected to the frame.

Example 8. The prosthetic heart valve of any example herein, particularly any of examples 1-7, wherein the sub-commissure tabs comprise lower sub-commissure tabs and wherein each leaflet comprises two opposing upper sub-commissure tabs arranged on opposite sides of the main body, wherein each upper sub-commissure tab is paired with an adjacent upper sub-commissure tab of an adjacent leaflet and connected thereto.

Example 9. The prosthetic heart valve of any example herein, particularly example 8, wherein each pair of upper sub-commissure tabs extends radially inwardly relative to the frame.

Example 10. The prosthetic heart valve of any example herein, particularly example 9, wherein each pair of upper sub-commissure tabs extends radially outwardly toward an inner surface of the frame.

Example 11. The prosthetic heart valve of any example herein, particularly any of examples 8-10, wherein the upper sub-commissure tabs of each pair of upper sub-commissure tabs are sutured to each other.

Example 12. The prosthetic heart valve of any example herein, particularly any of examples 8-11, wherein the pairs of upper sub-commissure tabs are not directly connected to the frame.

Example 13. The prosthetic heart valve of any example herein, particularly any of examples 8-12, wherein each upper sub-commissure tab is arranged between and spaced from an adjacent commissure tab and an adjacent lower commissure tab on one side of the corresponding leaflet.

Example 14. The prosthetic heart valve of any example herein, particularly any of examples 1-13, wherein each leaflet has two upper tabs connected to upper edges of the commissure tabs and folded downwardly against the commissure tabs.

Example 15. The prosthetic heart valve of any example herein, particularly any of examples 1-14, wherein the frame comprises a plurality of commissure support posts, and the commissures are mounted to the commissure support posts.

Example 16. The prosthetic heart valve of any example herein, particularly example claim 15, wherein the commissure support posts are components of actuators that are configured to produce radial expansion and compression of the frame.

Example 17. A method of assembling a prosthetic heart valve, comprising: providing a plurality of leaflets, wherein each leaflet comprises a main body, two opposing commissure tabs arranged on opposite sides of the main body and two opposing sub-commissure tabs arranged on opposite sides of the main body; pairing each commissure tab with an adjacent commissure of an adjacent leaflet to form a plurality of commissures, and coupling the commissures to an annular frame, wherein the frame is radially compressible and expandable between a radially compressed state and a radially expanded state; and pairing each sub-commissure tab with an adjacent commissure of an adjacent leaflet, wherein each pair of sub-commissure tabs extends radially inwardly relative to the frame.

Example 18. The method of any example herein, particularly example 17, wherein pairing each sub-commissure tab with an adjacent commissure of an adjacent leaflet comprises suturing the sub-commissure tabs of each pair to each other.

Example 19. The method of any example herein, particularly any of examples 17-18, further comprising coupling the cusp edge portion of each leaflet to the frame, wherein the cusp edge portion of each leaflet extends from one sub-commissure tab to the other sub-commissure tab of the leaflet.

Example 20. The method of any example herein, particularly example 19, further comprising suturing a first reinforcing member the cusp edge portions of the leaflets and to selected struts of the frame.

Example 21. The method of any example herein, particularly example 20, further comprising suturing a second reinforcement member to the cusp edge portions of the leaflets, wherein the first and second reinforcing members are positioned on opposite sides of the cusp edge portions of the leaflets.

Example 22. The method of any example herein, particularly any of examples 17-21, wherein the pairs of sub-commissure tabs are not directly connected to the frame.

Example 23. The method of any example herein, particularly any of examples 17-22, wherein the main body of each leaflet is formed with pair of notches, each of which extends between a commissure tab and a sub-commissure tab, wherein the notches are not directly connected to the frame.

Example 24. The method of any example herein, particularly any of examples 17-23, wherein the sub-commissure tabs comprise lower sub-commissure tabs and wherein each leaflet comprises two opposing upper sub-commissure tabs arranged on opposite sides of the main body, wherein the method further comprises connecting each upper sub-commissure tab to an adjacent upper sub-commissure tab of an adjacent leaflet to form pairs of upper sub-commissure tabs.

Example 25. The method of any example herein, particularly example 24, wherein each pair of upper sub-commissure tabs extends radially inwardly relative to the frame.

Example 26. The method of any example herein, particularly example 24, wherein each pair of upper sub-commissure tabs extends radially outwardly toward an inner surface of the frame.

Example 27. The method of any example herein, particularly any of examples 24-26, wherein connecting each upper sub-commissure tab to an adjacent upper sub-commissure tab comprises suturing the upper sub-commissure tabs of each pair to each other.

Example 28. The method of any example herein, particularly any of examples 24-27, wherein the pairs of upper sub-commissure tabs are not directly connected to the frame.

Example 29. The method of any example herein, particularly any of examples 24-28, wherein each upper sub-commissure tab is arranged between and spaced from an adjacent commissure tab and an adjacent lower commissure tab on one side of the corresponding leaflet.

Example 30. The method of any example herein, particularly any of examples 17-29, wherein each leaflet has two upper tabs connected to upper edges of the commissure tabs and the method comprises folding the upper tabs of each leaflet downwardly against the commissure tabs prior to coupling the commissures to the frame.

Example 31. The method of any example herein, particularly any of examples 17-30, wherein the frame comprises a plurality of commissure support posts, and coupling the commissures to the frame comprises mounting the commissures to the commissure support posts.

Example 32. The method of any example herein, particularly example 31, wherein the commissure support posts are components of actuators that are configured to produce radial expansion and compression of the frame.

Example 33. A prosthetic heart valve comprising: an annular frame comprising a plurality of interconnected struts, wherein the frame is radially compressible and expandable between a radially compressed state and a radially expanded state; and a plurality of leaflets situated within the frame, each leaflet comprising a main body, a cusp edge portion, two opposing commissure tabs arranged on opposite sides of the main body, two sub-commissures edges forming notches on opposite sides of the main body between the commissure tabs and upper end portions of the cusp edge portion, and two opposing sub-commissure tabs arranged on opposite sides of the main body and extending laterally from the sub-commissures edges; wherein each commissure tab of a leaflet is paired with an adjacent commissure tab of an adjacent leaflet to form a commissure that is coupled to the frame; wherein each sub-commissure tab is paired with an adjacent sub-commissure tab of an adjacent leaflet and connected thereto.

Example 34. The prosthetic heart valve of any example herein, particularly example 33, wherein each pair of sub-commissure tabs extends radially inwardly relative to the frame.

Example 35. The prosthetic heart valve of any example herein, particularly example 33, wherein each pair of sub-commissure tabs extends radially outwardly toward an inner surface of the frame.

Example 36. The prosthetic heart valve of any example herein, particularly any of examples 33-35, wherein the sub-commissure tabs of each pair of sub-commissure tabs are sutured to each other.

Example 37. The prosthetic heart valve of any example herein, particularly any of examples 33-36, wherein the pairs of sub-commissure tabs and the two sub-commissure edges are not directly connected to the frame.

Example 38. The prosthetic heart valve of any example herein, particularly any of examples 33-37, wherein each sub-commissure tab is arranged between and spaced from an adjacent commissure tab and an adjacent upper end portion of the cusp edge portion on one side of the corresponding leaflet.

Example 39. The prosthetic heart valve of any example herein, particularly any of examples 33-38, wherein the sub-commissure tabs comprises upper sub-commissure tabs, and wherein the upper end portions of the cusp edge portion of each leaflet comprise lower sub-commissure tabs arranged on opposite sides of the main body, wherein each lower sub-commissure tab is paired with an adjacent lower sub-commissure tab of an adjacent leaflet and connected thereto.

Example 40. The prosthetic heart valve of any example herein, particularly example 39, wherein the lower sub-commissure tabs of each pair of lower sub-commissure tabs are sutured to each other.

Example 41. The prosthetic heart valve of any example herein, particularly any of examples 39-40, wherein each pair of lower sub-commissure tabs extends radially inwardly relative to the frame.

Example 42. The prosthetic heart valve of any example herein, particularly any of examples 39-41, wherein the pairs of lower sub-commissure tabs are not directly connected to the frame.

Example 43. The prosthetic heart valve of any example herein, particularly any of examples 33-42, further comprising a first reinforcing member sutured to the cusp edge portions of the leaflets and to selected struts of the frame.

Example 44. The prosthetic heart valve of any example herein, particularly example 43, further comprising a second reinforcement member sutured to the cusp edge portions of the leaflets, wherein the first and second reinforcing members are positioned on opposite sides of the cusp edge portions of the leaflets.

Example 45. The prosthetic heart valve of any example herein, particularly any of examples 33-44, wherein each leaflet has two upper tabs connected to upper edges of the commissure tabs and folded downwardly against the commissure tabs.

Example 46. The prosthetic heart valve of any example herein, particularly any of examples 33-45, wherein the frame comprises a plurality of commissure support posts, and the commissures are mounted to the commissure support posts.

Example 47. The prosthetic heart valve of any example herein, particularly example 46, wherein the commissure support posts are components of actuators that are configured to produce radial expansion and compression of the frame.

Example 48. A method of assembling a prosthetic heart valve, comprising: providing a plurality of leaflets, wherein each leaflet comprises a main body, a cusp edge portion, two opposing commissure tabs arranged on opposite sides of the main body, two sub-commissures edges forming notches on opposite sides of the main body between the commissure tabs and upper end portions of the cusp edge portion, and two opposing sub-commissure tabs arranged on opposite sides of the main body and extending laterally from the sub-commissures edges; pairing each commissure tab with an adjacent commissure of an adjacent leaflet to form a plurality of commissures, and coupling the commissures to an annular frame, wherein the frame is radially compressible and expandable between a radially compressed state and a radially expanded state; and pairing each sub-commissure tab with an adjacent commissure of an adjacent leaflet and connecting the sub-commissure tabs of each pair to each other.

Example 49. The method of any example herein, particularly example 48, wherein each pair of sub-commissure tabs extends radially inwardly relative to the frame.

Example 50. The method of any example herein, particularly example 48, wherein each pair of sub-commissure tabs extends radially outwardly toward an inner surface of the frame.

Example 51. The method of any example herein, particularly any of examples 49-50, wherein connecting the sub-commissure tabs of each pair of sub-commissure tabs to each other comprises suturing the sub-commissure tabs of each pair of sub-commissure tabs to each other.

Example 52. The method of any example herein, particularly any of examples 48-51, further comprising coupling the cusp edge portion of each leaflet to the frame.

Example 53. The method of any example herein, particularly example 52, further comprising suturing a first reinforcing member the cusp edge portions of the leaflets and to selected struts of the frame Example 54. The method of any example herein, particularly example 53, further comprising suturing a second reinforcement member to the cusp edge portions of the leaflets, wherein the first and second reinforcing members are positioned on opposite sides of the cusp edge portions of the leaflets.

Example 55. The method of any example herein, particularly any of examples 48-54, wherein the pairs of sub-commissure tabs and the two sub-commissure edges are not directly connected to the frame.

Example 56. The method of any example herein, particularly any of examples 48-55, wherein each sub-commissure tab is arranged between and spaced from an adjacent commissure tab and an adjacent upper end portion of the cusp edge portion on one side of the corresponding leaflet.

Example 57. The method of any example herein, particularly any of examples 48-56, wherein the sub-commissure tabs comprises upper sub-commissure tabs, and wherein the upper end portions of the cusp edge portion of each leaflet comprise lower sub-commissure tabs arranged on opposite sides of the main body, wherein the method further comprises connecting each lower sub-commissure tab to an adjacent lower sub-commissure tab of an adjacent leaflet to form pairs of lower sub-commissure tabs.

Example 58. The method of any example herein, particularly example 57, wherein connecting each lower sub-commissure tab to an adjacent lower sub-commissure tab of an adjacent leaflet comprises suturing the lower sub-commissure tabs of each pair of lower sub-commissure tabs to each other.

Example 59. The method of any example herein, particularly any of examples 57-58, wherein each pair of lower sub-commissure tabs extends radially inwardly relative to the frame.

Example 60. The method of any example herein, particularly any of examples 57-59, wherein the pairs of lower sub-commissure tabs are not directly connected to the frame.

Example 61. The method of any example herein, particularly any of examples 48-60, wherein each leaflet has two upper tabs connected to upper edges of the commissure tabs and the method comprises folding the upper tabs of each leaflet downwardly against the commissure tabs prior to coupling the commissures to the frame.

Example 62. The method of any example herein, particularly any of examples 48-61, wherein the frame comprises a plurality of commissure support posts, and coupling the commissures to the frame comprises mounting the commissures to the commissure support posts.

Example 63. The method of any example herein, particularly example 62, wherein the commissure support posts are components of actuators that are configured to produce radial expansion and compression of the frame.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic heart valve comprising:

an annular frame comprising a plurality of interconnected struts, wherein the frame is radially compressible and expandable between a radially compressed state and a radially expanded state, wherein the frame comprises an inflow end and an outflow end, the inflow end being upstream of the outflow end; and a plurality of leaflets situated within the frame, each leaflet comprising a main body, an inflow edge portion, two opposing commissure tabs arranged on opposite sides of the main body, two opposing sub-commissure tabs arranged on opposite sides of the main body, and two notches on opposite sides of the main body, wherein the sub-commissure tabs are located upstream and separated from the commissure tabs by the notches;

wherein:

(i) each commissure tab of a leaflet is paired with an adjacent commissure tab of an adjacent leaflet to form a commissure that is coupled to the frame;

(ii) each sub-commissure tab is paired with an adjacent sub-commissure tab of an adjacent leaflet and connected thereto, wherein each pair of sub-commissure tabs extends radially inwardly relative to the frame or radially outwardly relative to the frame; and (iii) the leaflets open under a forward flow of blood through the prosthetic heart valve in a direction from the inflow end of the frame to the outflow end of the frame and close under a reverse flow of blood.

2. The prosthetic heart valve of claim 1, wherein the sub-commissure tabs of each pair of sub-commissure tabs are sutured to each other.

3. The prosthetic heart valve of claim 1, wherein the inflow edge portion of each leaflet extends from one sub-commissure tab to the other sub-commissure tab of the leaflet, wherein the cusp edge portion is coupled to the frame.

4. The prosthetic heart valve of claim 3, further comprising a first reinforcing member sutured to the cusp edge portions of the leaflets and to selected struts of the frame.

5. The prosthetic heart valve of claim 4, further comprising a second reinforcing member sutured to the cusp edge portions of the leaflets, wherein the first and second reinforcing members are positioned on opposite sides of the cusp edge portions of the leaflets.

6. The prosthetic heart valve of claim 1, wherein the pairs of sub-commissure tabs are not directly connected to the frame.

7. The prosthetic heart valve of claim 1, wherein each notch extends between a commissure tab and a sub-commissure tab, wherein the notches are not directly connected to the frame.

8. The prosthetic heart valve of claim 1, wherein the sub-commissure tabs comprise lower sub-commissure tabs and wherein each leaflet comprises two opposing upper sub-commissure tabs arranged on opposite sides of the main body, wherein each upper sub-commissure tab is paired with an adjacent upper sub-commissure tab of an adjacent leaflet and connected thereto.

9. The prosthetic heart valve of claim 8, wherein each pair of upper sub-commissure tabs extends radially inwardly relative to the frame.

10. The prosthetic heart valve of claim 8, wherein each pair of upper sub-commissure tabs extends radially outwardly toward an inner surface of the frame.

11. The prosthetic heart valve of claim 8, wherein the upper sub-commissure tabs of each pair of upper sub-commissure tabs are sutured to each other.

12. The prosthetic heart valve of claim 8, wherein the pairs of upper sub-commissure tabs are not directly connected to the frame.

13. The prosthetic heart valve of claim 8, wherein each upper sub-commissure tab is arranged between and spaced from an adjacent commissure tab and an adjacent lower sub-commissure tab on one side of the corresponding leaflet.

14. The prosthetic heart valve of claim 1, wherein each leaflet has two upper tabs connected to upper edges of the commissure tabs and folded downwardly against the commissure tabs.

15. The prosthetic heart valve of claim 1, wherein the frame comprises a plurality of commissure support posts, and the commissures are mounted to the commissure support posts.

16. The prosthetic heart valve of claim 15, wherein the commissure support posts are components of actuators that are configured to produce radial expansion and compression of the frame.

17. A method of assembling a prosthetic heart valve, comprising:

providing an annular frame comprising a plurality of interconnected struts, wherein the frame is radially compressible and expandable between a radially compressed state and a radially expanded state, wherein the frame comprises an inflow end and an outflow end, the inflow end being upstream of the outflow end;

providing a plurality of leaflets, wherein each leaflet comprises a main body, an inflow edge portion, two opposing commissure tabs arranged on opposite sides of the main body, two opposing sub-commissure tabs arranged on opposite sides of the main body, and two notches on opposite sides of the main body, wherein the sub-commissure tabs are located upstream and separated from the commissure tabs by the notches;

pairing each commissure tab of a leaflet with an adjacent commissure tab of an adjacent leaflet to form a plurality of commissures, and coupling the commissures to the annular frame; and pairing each sub-commissure tab of a leaflet with an adjacent sub-commissure tab of an adjacent leaflet and connecting the paired sub-commissure tabs to each other, wherein each pair of sub-commissure tabs extends radially inwardly relative to the frame or radially outwardly relative to the frame;

wherein the leaflets open under a forward flow of blood through the prosthetic heart valve in a direction from the inflow end of the frame to the outflow end of the frame and close under a reverse flow of blood.

18. The method of claim 17, wherein connecting the paired sub-commissure tabs comprises suturing the sub-commissure tabs of each pair to each other.

19. The method of any of claim 17, further comprising coupling the inflow edge portion of each leaflet to the frame, wherein the inflow edge portion of each leaflet extends from one sub-commissure tab to the other sub-commissure tab of the leaflet.

20. The method of claim 19, further comprising suturing a first reinforcing member to the inflow edge portions of the leaflets and to selected struts of the frame.

21. The method of claim 20, further comprising suturing a second reinforcement member to the inflow edge portions of the leaflets, wherein the first and second reinforcing members are positioned on opposite sides of the inflow edge portions of the leaflets.

22. The method of claim 17, wherein the pairs of sub-commissure tabs are not directly connected to the frame.

23. A prosthetic heart valve comprising:

an annular frame comprising a plurality of interconnected struts, wherein the frame is radially compressible and expandable between a radially compressed state and a radially expanded state, wherein the frame comprises an inflow end and an outflow end, wherein the inflow end is upstream of the outflow end; and a plurality of leaflets situated within the frame, each leaflet comprising a main body, a cusp edge portion, two opposing commissure tabs arranged on opposite sides of the main body, two sub-commissure edges forming notches on opposite sides of the main body between the commissure tabs and upper end portions of the cusp edge portion, and two opposing sub-commissure tabs arranged on opposite sides of the main body and extending laterally from the sub-commissures edges, wherein the sub-commissure tabs are located upstream and separated from the commissure tabs by the notches;

wherein:

(i) each commissure tab of a leaflet is paired with an adjacent commissure tab of an adjacent leaflet to form a commissure that is coupled to the frame;

(ii) each sub-commissure tab is paired with an adjacent sub-commissure tab of an adjacent leaflet and connected thereto; and (iii) the leaflets open under a forward flow of blood through the prosthetic heart valve in a direction from the inflow end of the frame to the outflow end of the frame and close under a reverse flow of blood.

24. The prosthetic heart valve of claim 23, wherein each pair of sub-commissure tabs extends radially inwardly relative to the frame.

25. The prosthetic heart valve of claim 23, wherein each pair of sub-commissure tabs extends radially outwardly toward an inner surface of the frame.

26. The prosthetic heart valve of claim 23, wherein the sub-commissure tabs of each pair of sub-commissure tabs are sutured to each other.

27. The prosthetic heart valve of claim 23, wherein the pairs of sub-commissure tabs and the two sub-commissure edges are not directly connected to the frame.

28. The prosthetic heart valve of claim 23, wherein each sub-commissure tab is arranged between and spaced from an adjacent commissure tab and an adjacent upper end portion of the cusp edge portion on one side of the corresponding leaflet.

29. The prosthetic heart valve of claim 23, wherein the sub-commissure tabs comprises upper sub-commissure tabs, and wherein the upper end portions of the cusp edge portion of each leaflet comprise lower sub-commissure tabs arranged on opposite sides of the main body, wherein each lower sub-commissure tab is paired with an adjacent lower sub-commissure tab of an adjacent leaflet and connected thereto.

30. The prosthetic heart valve of claim 29, wherein the lower sub-commissure tabs of each pair of lower sub-commissure tabs are sutured to each other.

* * * * *